US005596086A

United States Patent [19]

Matteucci et al.

[11] Patent Number: 5,596,086

[45] Date of Patent: Jan. 21, 1997

[54] MODIFIED INTERNUCLEOSIDE LINKAGES HAVING ONE NITROGEN AND TWO CARBON ATOMS

[75] Inventors: Mark Matteucci, Burlingame; Robert J. Jones, Daly City; John Munger, San Francisco, all of Calif.

[73] Assignee: Gilead Sciences, Inc., Foster City, Calif.

[21] Appl. No.: 763,130

[22] Filed: Sep. 20, 1991

Related U.S. Application Data

[63] Continuation-in-part of Ser. No. 585,780, Sep. 20, 1990, abandoned.

[51] Int. Cl.$^6$ .......................... C07H 21/00; C07H 21/02; C07H 21/04; A61K 31/70

[52] U.S. Cl. ......................... 536/22.1; 536/24.3; 536/24.5

[58] Field of Search ................................ 536/27, 28, 29, 536/23-24, 26, 22.1, 23.1

[56] References Cited

U.S. PATENT DOCUMENTS

| | | | |
|---|---|---|---|
| 5,138,045 | 8/1992 | Cook et al. . | |
| 5,223,618 | 6/1993 | Cook et al. | 544/276 |
| 5,378,825 | 1/1995 | Cook et al. | 536/25.34 |

FOREIGN PATENT DOCUMENTS

| | | |
|---|---|---|
| WO89/11486 | 11/1989 | WIPO . |
| WO89/12060 | 12/1989 | WIPO . |

OTHER PUBLICATIONS

Zon, G., "Oligonucleotide Analogues as Potential Chemotherapeutic Agents," PHARM RES 5:539–549 (1988).

Alan W. Schwartz and Leslie E. Orgel, "Template-Directed Synthesis of Novel, Nucleic Acid-Like Structures", *Science*, vol. 228, (May 3, 1985), pp. 585–587.

Agarwal and Riftina, *Nucleic Acids Res.* (1979) 6:3009–3024.

Agarwal et al., *Proc. Natl. Acad. Sci.* (1988) 85:7079–7083.

Uhlmann and Peyman, *Chemical Reviews* (1990) 90:543–584.

Coull et al., *Tetrahedron Letters* (1987) 28(7):745–748.

Stirchak and Summerton, *J. Organ. Chem.* (1987) 52:4202–4206.

Cosstick and Vyle, *Tetrahedron Letters* (1989) 30(35):4693–4696.

van der Krol et al., *Biotechniques* (1988) 6(10):958–976.

Stein and Cohen, *Cancer Res.* (1988) 48:2659–2668.

Matteucci, *Tetrahedron Letters* (1990) 31(17):2385–2388.

Miller et al., *Biochemistry* (1981) 20:1874–1880.

*Primary Examiner*—Gary L. Kunz

*Attorney, Agent, or Firm*—Daryl D. Muenchau

[57] ABSTRACT

Oligonucleotide analogs are disclosed wherein one or more phosphodiester linkages between adjacent nucleotides are replaced by a backbone linkage resistant to nucleases. The modified oligonucleotides are capable of strong hybridization to target RNA or DNA. The oligomers of the invention may be used as diagnostic reagents to detect the presence or absence of the target DNA or RNA sequences to which they bind.

12 Claims, 18 Drawing Sheets

6

7

8

9

22 23 24

25 26 27 28

5 29 30

31 Step 1 32 Step 2 33

12 34

35

21 5 36

37

38 39 12

40 41

42 43 44 45

15 46

47 48 49

50 51 52

39 53 54

54 45 55

55 56 57

58 59 60

21 61 62 63

64 65 66

67 68 69

46 70 or 77 78

71 72

4 73

31 74

75 76

10

80

16

81;R=$CH_3$
82;R=$CH_3(CH_2)_4$
83;R=$CH_3OCH_2$

84;R=$CH_3$
85;R=$CH_3(CH_2)_4$
86;R=$CH_3OCH_2$

87;R=$CH_3$
88;R=$CH_3(CH_2)_4$
89;R=$CH_3OCH_2$

90

91

92;R=$CH_3CH_2$
93;R=$CH_3(CH_2)_5$

94;R=$CH_3CH_2$
95;R=$CH_3(CH_2)_5$ 96 97 98

80

99 100 31

101 102

46 103 42

104 105

MODIFIED INTERNUCLEOSIDE LINKAGES HAVING ONE NITROGEN AND TWO CARBON ATOMS

CROSS-REFERENCE TO RELATED APPLICATION

This is a continuation-in-part of U.S. patent application Ser. No. 07/585,780, filed Sep. 20, 1990, now abandoned, from which priority is claimed under 35 U.S.C. §120 and which is incorporated herein by reference in its entirety.

TECHNICAL FIELD

The invention relates to novel modified oligonucleotides, the construction thereof and their use in. More specifically, the invention concerns novel oligonucleotides with modified internucleoside linkages which are resistant to nucleases, and are capable of binding target oligonucleotide sequences in vitro.

BACKGROUND ART

Antisense oligonucleotides are synthetic oligonucleotides which bind complementary nucleic acids (i.e. sense strand sequences) via hydrogen bonding, thereby inhibiting translation of these sequences. Therapeutic intervention at the nucleic acid level using antisense oligonucleotides offers a number of advantages. For example, gene expression can be inhibited using antisense oligomers. Inhibition of gene expression is more efficient than inhibition of the protein encoded by the gene since transcription of a single DNA sequence gives rise to multiple copies of mRNA which, in turn, are translated into many protein molecules.

Antisense therapies for diseases whose etiology is characterized by, or associated with, specific DNA or RNA sequences, is particularly useful. The oligomer employed as the therapeutic agent can be directly administered or generated in situ and is one that is complementary to a DNA or RNA needed for the progress of the disease. The oligomer specifically binds to this target nucleic acid sequence, thus disturbing its ordinary function.

An oligomer having a base sequence complementary to that of an mRNA which encodes a protein necessary for the progress of the disease, is particularly useful. By hybridizing specifically to this mRNA, the synthesis of the protein will be interrupted. However, it is also possible to bind double-stranded DNA using an appropriate oligomer capable of effecting the formation of a specific triple helix by inserting the administered oligomer into the major groove of the double-helical DNA. The elucidation of the sequences which form the targets for the therapeutics is, of course, a problem which is specific to each target condition or disease. While the general principles are well understood and established, a great deal of preliminary sequence information is required for the design of a particular oligomeric probe.

An important feature of the antisense oligomeric probes is the design of the backbone of the administered oligomer. Specifically, the backbone should contain internucleoside linkages that are stable in vivo and should be structured such that the oligomer is resistant to endogenous nucleases, such as nucleases that attack the phosphodiester linkage. At the same time, the oligomer must also retain its ability to hybridize to the target DNA or RNA. (Agarwal, K. L. et al., *Nucleic Acids Res* (1979) 6:3009; Agarwal, S. et al., *Proc Natl Acad Sci USA* (1988) 85:7079.) In order to ensure these properties, a number of modified oligonucleotides have been constructed which contain alternate internucleoside linkages. Several of these oligonucleotides are described in Uhlmann, E. and Peyman, A., *Chemical Reviews* (1990) 90:543–584. Among these are methylphosphonates (wherein one of the phosphorous-linked oxygens has been replaced by methyl); phosphorothioates (wherein sulphur replaces one of these oxygens) and various amidates (wherein $NH_2$ or an organic amine derivative, such as morpholidates or piperazidates, replace an oxygen). These substitutions confer enhanced stability, for the most part, but suffer from the drawback that they result in a chiral phosphorous in the linkage, thus leading to the formation of $2^n$ diastereomers where n is the number of modified diester linkages in the oligomer. The presence of these multiple diastereomers considerably weakens the capability of the modified oligonucleotide to hybridize to target sequences. Some of these substitutions also retain the ability to support a negative charge and the presence of charged groups decreases the ability of the compounds to penetrate cell membranes. There are numerous other disadvantages associated with these modified linkages, depending on the precise nature of the linkage.

It has also been suggested to use carbonate diesters. However, these are highly unstable, and the carbonate diester link does not maintain a tetrahedral configuration exhibited by the phosphorous in the phosphodiester. Similarly, carbamate linkages, while achiral, confer trigonal symmetry and it has been shown that poly dT having this linkage does not hybridize strongly with poly dA (Coull, J. M., et al., *Tet Lett* (1987) 28:745; Stirchak, E. P., et al., *J Org Chem* (1987) 52:4202.

Commonly owned, pending U.S. patent application Ser. No. 557,957, filed 30 Jul. 1990, describes modified linkages of the formula —$YCX_2Y$— wherein Y is independently O or S and wherein each X is a stabilizing substituent and independently chosen.

The general approach to constructing oligomers useful in antisense therapy has been reviewed, for example, by Uhlmann, E. and Peyman, A., *Chemical Reviews* (1990) 90:543–584; van der Krol, A. R., et al., *Biotechniques* (1988 6:958–976; and by Stein, C. A. et al., *Cancer Res* (1988) 48:2659–2668, all incorporated herein by reference in their entirety.

The present invention provides an internucleoside linkage which is resistant to nuclease digestion, and which is stable under physiological conditions, and which can be neutral or positively charged so as to enhance cell permeation. Furthermore, the linkages can be achiral and thus do not lead to the problem of multiple diastereomers in the resulting compounds.

DISCLOSURE OF THE INVENTION

The present invention is based on the construction of novel oligonucleotides containing modified backbone linkages also referred to as modified internucleoside linkages. These oligonucleotides are stable in vivo, resistant to endogenous nucleases and are able to hybridize to target nucleotide sequences.

In one embodiment, the present invention is directed to a modified oligonucleotide or derivative thereof, wherein the modification comprises substitution, for one or more phosphodiester linkages between 3' and 5' adjacent nucleosides, with a two to four atom long internucleoside linkage wherein at least one of the atoms making up the internucleoside linkage is selected from nitrogen, oxygen and sulfur, with the remainder being carbon.

In another embodiment, the subject invention is directed to an oligomer of the formula

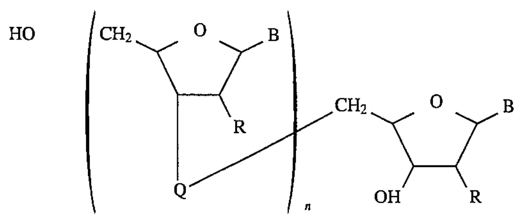

(1)

or a derivative thereof, wherein each R is independently H, OH, $OCH_3$, $SCH_3$, $OC_3H_5$(O-allyl)$OC_3H_7$(O-propyl), $SC_3H_5$ or F, and wherein each B is independently a purine or pyrimidine residue or an analogous residue, and wherein each Q is independently a phosphodiester analog or a two to four atom long internucleoside linkage wherein at least one of the atoms making up the internucleoside linkage is selected from nitrogen, oxygen or sulfur, with the remainder being carbon; n is 1–200;

subject to the proviso that at least one Q is not a phosphodiester analog.

These and other embodiments of the present invention will readily occur to those of ordinary skill in the art in view of the disclosure herein.

BRIEF DESCRIPTION OF THE FIGURES

FIG. 1 shows the formation of a three atom long linkage with a nitrogen at the 5' end.

FIG. 2 shows the formation of a three atom long linkage with a nitrogen at the 3' end.

FIG. 3 depicts the formation of a three atom long linkage with a nitrogen in the middle.

FIG. 4 depicts the formation of a four atom long linkage with oxygen at the 3' end and nitrogen at the 5' end.

FIG. 5 shows the formation of a four atom long linkage with nitrogen at the 3' end and oxygen at the 5' end.

FIG. 6 depicts the formation of a two atom long linkage with nitrogen at the 5' end.

FIG. 7 shows the formation of a two atom long linkage with nitrogen at the 3' end.

FIG. 8 shows the formation of three different three atom long linkages with sulfur at the 3' end.

FIG. 9 depicts the formation of three different two atom long linkages with sulfur at the 3' end.

FIG. 10 shows the formation of three different two atom long linkages with sulfur at the 5' end.

FIG. 11 depicts the formation of a three atom long linkage with oxygen at the 3' end.

FIG. 12 depicts the formation of a three atom long linkage with oxygen at the 5' end.

FIG. 13 shows the formation of a three atom long linkage with derivatized nitrogen at the 3' end.

FIG. 14 shows the formation of a morpholino-containing linkage.

FIG. 15 shows the formation of a three atom long linkage with sulfur at the 3' end.

DETAILED DESCRIPTION

Figure 1:
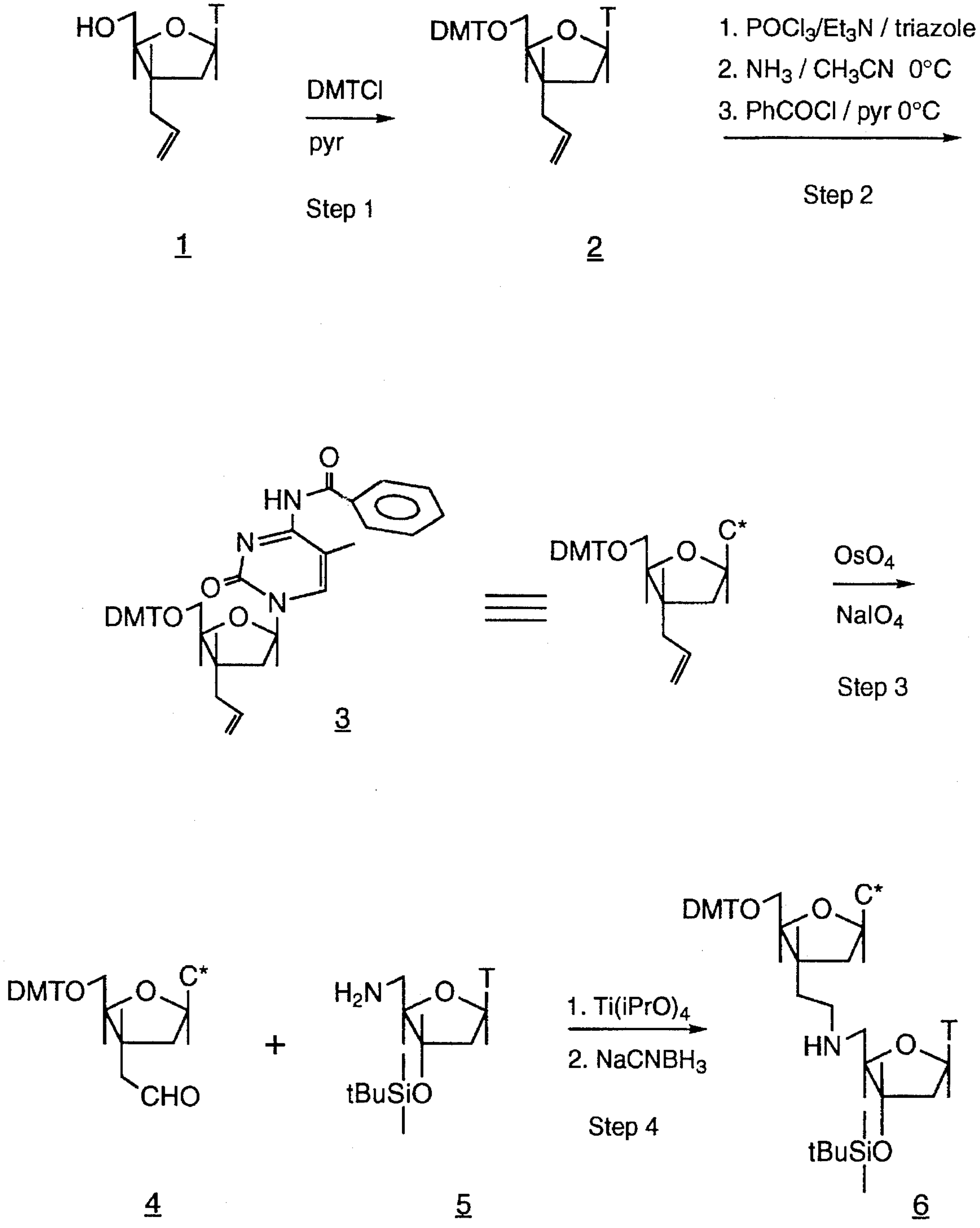
FIGS. 1 through 15 are depictions of twelve chemical reaction sequences usable for synthesizing internucleoside linkages of the present invention. More specifically.
Figure 1:
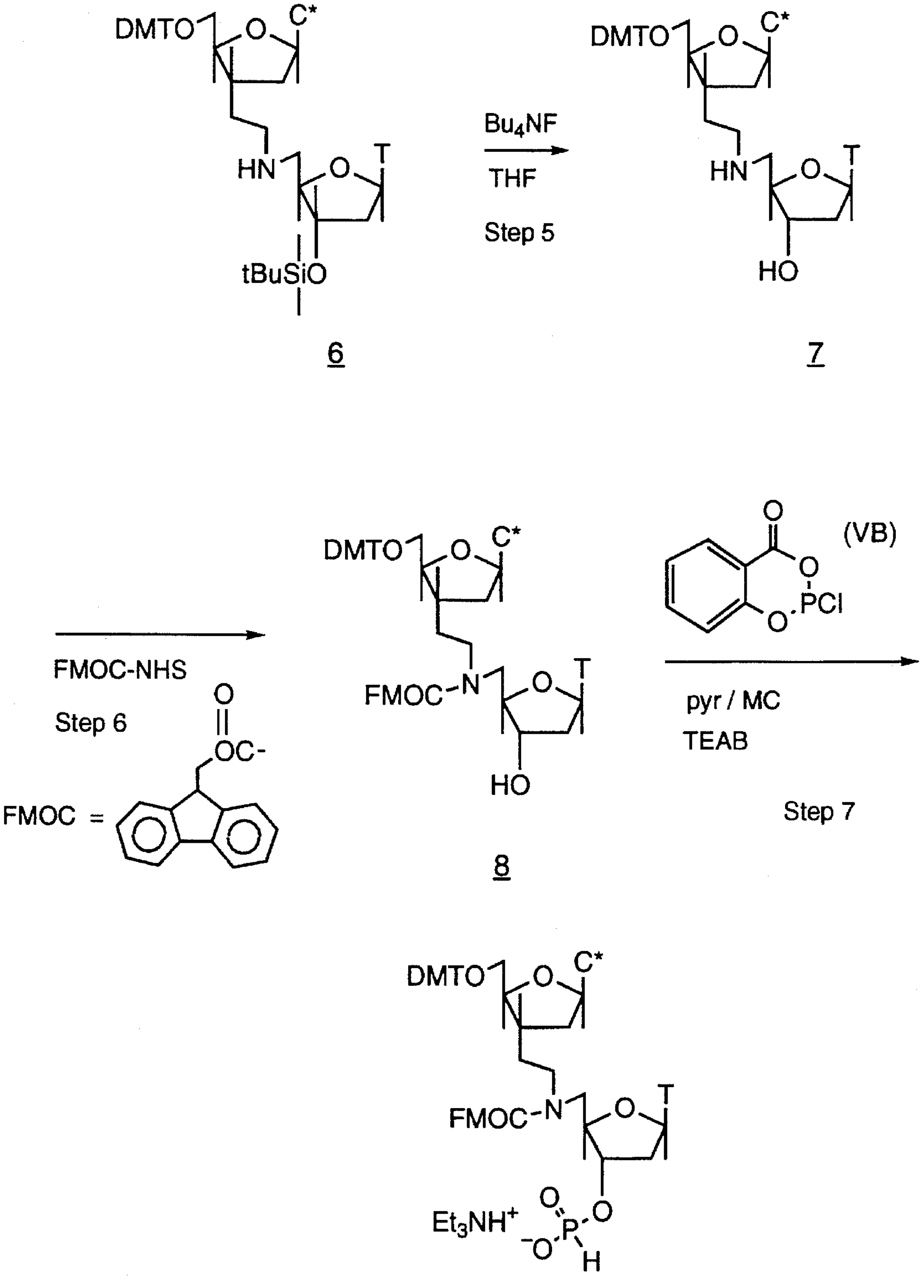

The practice of the present invention will employ, unless otherwise indicated, conventional techniques of chemistry, molecular biology, biochemistry, protein chemistry, and recombinant DNA technology, which are within the skill of the art. Such techniques are explained fully in the literature. See, e.g., *Oligonucleotide Synthesis* (M. J. Gait ed. 1984); *Nucleic Acid Hybridization* (B. D. Hames & S. J. Higgins eds. 1984); Sambrook, Fritsch & Maniatis, *Molecular Cloning: A Laboratory Manual,* Second Edition (1989); and the series *Methods in Enzymology* (S. Colowick and N. Kaplan eds., Academic Press, Inc.).

A. Definitions

In describing the present invention, the following terms will be employed, and are intended to be defined as indicated below.

The binding may be by conventional base pair complementarity, or, for example, in the case of binding to DNA duplexes, through specific interactions in the major groove of the double helix.

"Oligomers" or "oligonucleotides" include both RNA and DNA sequences (both single and double stranded) of more than one nucleotide.

"Nucleoside" refers to a sugar or derivative thereof, as described further below, carrying a purine, pyrimidine, or analogous forms thereof, as defined below, but lacking a linking sequence such as a phosphodiester analog or a modified internucleoside linkage. By "5'" nucleoside is meant the nucleoside which provides the 5' carbon coupling point to the linker. The "5'" end of the linker couples to the 5' nucleoside. The "3'" end of the linker joins to the 3' position on the next nucleoside. If a modified nucleoside is present which does not precisely include a 3' and/or a 5' carbon, it is to be understood that this "3'" and "5'" terminology will be used by analogy.

"Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be (but need not be) derivatized through the modified backbone linkage as part of the linkage itself. For example, intercalators, such as acridine can be linked through an —R—$CH_2$—R— attached through any available —OH or —SH, e.g., at the terminal 5' position of RNA or DNA, the 2' positions of RNA, or an OH or SH engineered into the 5 position of pyrimidines, e.g., instead of the 5 methyl of cytosine, a derivatized form which contains —$CH_2CH_2CH_2OH$ or —$CH_2CH_2CH_2SH$ in the 5 position. A wide variety of substituents can be attached, including those bound through conventional linkages. Accordingly the indicated —OH moieties in the oligomer of formula (1) may be replaced by phosphonate groups, protected by standard protecting groups, or activated to prepare additional linkages to other nucleotides, or may be bound to the conjugated substituent. The 5' terminal OH is conventionally phosphorylated; the 2'—OH or OH substituents at the 3' terminus may also be phosphorylated. The hydroxyls may also be derivatized to standard protecting groups. In addition, specifically included are the 2'-derivatized forms of the nucleotide residues disclosed in commonly owned, copending U.S. application Ser. No. 425,857, as well as the formacetal/ketal type linkages disclosed in commonly owned, copending U.S. patent application Ser. No. 557,957, both incorporated herein by reference in their entirety. Synthesis of DNA oligomers and nucleosides with 2' modifications has been described for 2' fluoro compounds (Uesugi, S. et al., *Biochemistry* (1981) 20:3056–3062; Codington, J. F. et al., *J Organic Chem* (1964) 29:564–569; Fazakerley, G. V. et al., *FEBS Letters* (1985) 182:365–369), 2'—O—allyl compounds ($OC_3H_5$) (Sproat, B. S. et al., *Nucleic Acids Res* (1991) 19:733–738 and 2'-azido compounds (Hobbs, J. et al., Biochemistry (1973) 12:5138–5145). These derivatives are also specifically included.

Specific modifications that are contemplated for oligomers described in the present invention include moieties that permit duplex strand switching as described in commonly owned, pending U.S. patent application Ser. No. 690,786 now U.S. Pat. No. 5,264,562, moieties such as $N^4$ $N^4$-ethanocytosine (aziridinylcytosine) that affect covalent crosslinking as described in commonly owned, U.S. patent application Ser. No. 640,654, now abandoned, and moieties such as the base analog 8-hydroxy-$N^6$-methyladenine that facilitate oligomer binding to duplex target nucleic acid as described in commonly owned, U.S. patent application Ser. No. 643,382, now abandoned. The cited applications are incorporated herein by reference.

By "phosphodiester analog" is meant an analog of the conventional phosphodiester linkage

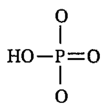

as well as alternative linking groups. These alternative linking groups include, but are not limited to embodiments wherein the HO—P=O(P(O)OH) is replaced with P(O)S, P(O)NR($R^1$), P(O)$R^2$, P(O)O$R^2$, CO or CN$R^2$, wherein $R^2$ is H or alkyl (1-6C) and $R^2$ is alkyl (1-6C). Not all phosphodiester analogs in the same oligomer need be identical, the only requirement being that at least one of these linkages is a modified internucleoside linkage as described herein. Also included in the definition of "derivatives" are substances wherein the conventional ribose sugar is replaced with heterocyclic compounds such as morpholine, as depicted in formula (2).

Formula 2

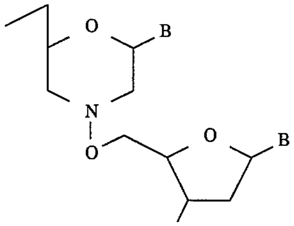

These derivatives are referred to herein as "morpholineB" wherein the B represents the derivatized base.

"Analogous" forms of purines and pyrimidines are those generally known in the art, many of which are used as chemotherapeutic agents. An exemplary but not exhaustive list includes 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A particularly preferred analog is 5-methylcytosine (abbreviated herein as "Cme").

"Isosteric" is used to describe the spatial and orientation properties of an internucleoside linkage and the fact that these properties are so similar to those of the native phosphodiester linkage that the modified oligonucleotide containing an isosteric bond will replace, substitute for, mimic and/or hybridize with a native oligonucleotide.

The invention is directed to new compounds and intermediates in their production, as well to methods to synthesize these compounds and their intermediates. In general, the invention compounds show enhanced stability with respect to nucleases by virtue of their modified linkages, as well as enhanced ability to permeate cells.

In a modified oligonucleotide of this invention, at least one of the phosphodiester groups included within the Qs of Formula 1 is substituted by the modified internucleoside linkages described herein. Desirably, multiple phosphodiester linkages in the unmodified oligonucleotides are substituted by the modified backbone linkages described herein. One modified internucleoside linkage may be used repeatedly in this structure, or, if desired a variety of modified internucleoside linkages may be used. Though it is preferred that these substituent linkages be non-chiral in nature to enhance the ability to hybridize, useful compounds of the invention can include those where chiral forms are used.

The linking moiety, Q, comprises a substitution, for one or more linkages between adjacent 3' and 5' nucleosides, with a two to four atom long internucleoside linkage wherein at least one of the atoms making up the internucleoside linkage are selected from nitrogen, oxygen or sulfur, with the remainder being carbon. Often, at least one of the two to four atoms is nitrogen in the form of NR, wherein R is hydrogen, lower alkyl, heteroalkyl, aryl, sulfonamide, phosphoramidate, NR', OR',

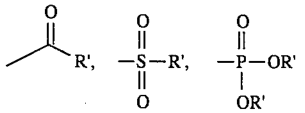

wherein R' is hydrogen, lower alkyl, heteroalkyl or aryl.

Preferred modified internucleoside linkages include the structures for Q shown in Table 1.

TABLE 1

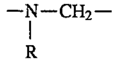

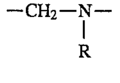

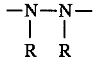

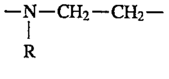

TABLE 1-continued
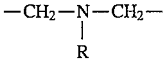
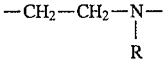
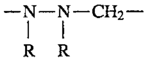
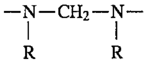
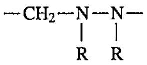
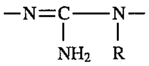
$-O-CH_2-$
$-CH_2-O-$
$-O-CH_2-CH_2-$
$-CH_2-O-CH_2-$
$-CH_2-CH_2-O-$
$-S-CH_2-$
$-CH_2-S-$
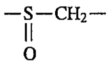
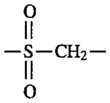
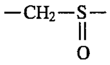
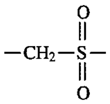
$-S-CH_2-CH_2-$
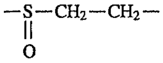
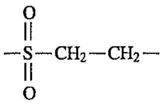
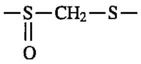
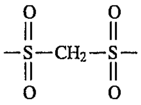
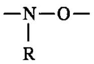
TABLE 1-continued
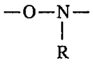
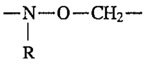
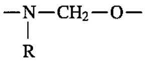
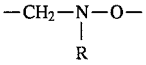
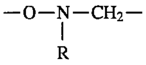
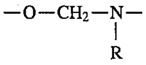
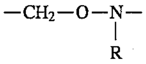
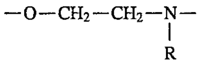
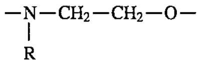
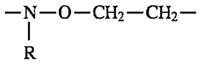
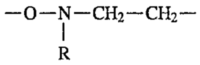
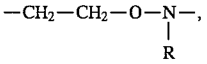, and
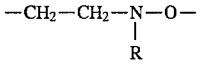
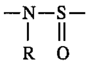
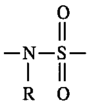
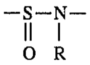
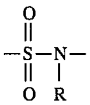
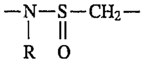
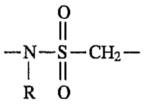

TABLE 1-continued

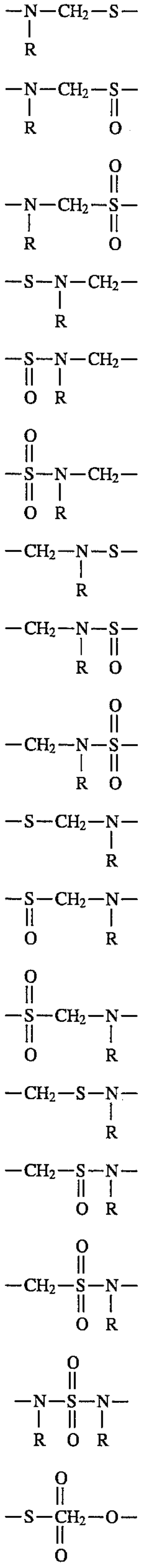

TABLE 1-continued

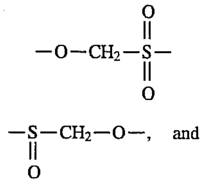

and

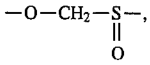

wherein R is as previously defined.

Particularly preferred internucleoside linkages include —$CH_2$—$CH_2$—NR—, —NR—$CH_2$—$CH_2$—, —$CH_2$—NR—$CH_2$—, —$CH_2CH_2$—$_2$—O—, —$CH_2$—O—$CH_2$—, —S—$CH_2$—$CH_2$—, and —O—$CH_2$—$CH_2$—NR—.

It should be clear that the invention compounds are not limited to oligomers of homogeneous linkage type, and that alternating or randomly distributed phosphodiester analogs and the modified backbone linkages are contemplated. Since the oligomers of the invention can be synthesized one nucleotide residue at a time, each individual linkage, and the nature of each individual "B" substituent can be chosen at will.

The Q linkages should be stable. The extent to which the spectrum of substituents present in the Q linkages can be extended can readily be determined by simple assays of stability of the resulting product, and this determination, and a good deal of predictability of the tolerance of these linkages, is within the ordinary skill of the art.

It should further be noted that if Q, itself, contains a functional group, Q can be used to tether desired moieties, for example, intercalators or minor groove reactive materials, such as netropsin and its derivatives, anthramycin, quinoxaline antibiotics, actinomycin, and pyrrolo (1–4) benzodiazepine derivatives.

The oligomers of the invention may contain an arbitrary number of the modified internucleoside linkages of the invention. These may be identical to each other or different by virtue of the embodiments chosen for Q. Since the oligomers are prepared sequentially, any pattern of linkage types, base substituents, and saccharide residues may be used.

In some preferred embodiments, the modified internucleoside linkages alternate in a regular pattern. For example, one modified linker followed by two phosphodiester analog linkages followed by one modified linker, etc. Additional alternatives might include, for example, alternating linkages such as a modified linkage followed by a phosphodiester analog followed by a modified linkage followed by a phosphodiester analog, etc., so that there is a one-by-one alternation of the two types of linkages. A variety of regularly variant patterns is readily derived.

It is also clear that arbitrary modifications may be made to one or more of these saccharide residues; however, for the most part, the standard 3'-5' nucleotide linkage between ribosyl residues is most convenient. Where this is the case, further abbreviation of the structures may be used. For example, in standard DNA (or RNA) the sequences are generally denoted by the sequence of bases alone, such as, for example, ATG CGC TGA. In general, it is simply stated in advance whether this represents an RNA or DNA sequence. In the compounds of the invention, similar notation will be used for modifications of otherwise physiological DNA or RNA molecules but the phosphodiester linkages replaced by the modified backbone linkages will be noted in the structure. Thus, 5'—TCTCme(O—$CH_2$—$CH_2$—NH)TCme(O—$CH_2$—$CH_2$—NH)TCme(O—$CH_2$—$CH_2$—NH)TCme(O—$CH_2$—$CH_2$—NH)TTTT—3' indicates an oligonucleotide TCTCmeTCmeTCmeTCmeTTTT (the Cme denoting 5-methylcytosine) with four of the phosphodiester linkages replaced in the noted positions.

B. Utility and Administration

The modified oligomers of the invention are isosteric with native oligonucleotides. This property enables them to hybridize with native sequences and thus makes them useful as hybridization probes for identifying such native sequences.

The modified oligomers of the invention are, as stated above, also useful in applications in antisense therapy.

Accordingly, the modified oligomers of the invention are useful, diagnostic and research contexts.

Accordingly, the modified oligomers of the invention are useful in, diagnostic and research contexts.

In addition, the oligomers of the invention may be used as diagnostic reagents to detect the presence or absence of the target DNA or RNA sequences to which they specifically bind. Such diagnostic tests are conducted by hybridization through base complementarity or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known. The oligomers of the invention are characterized by their ability to target specific oligonucleotide sequences regardless of the mechanisms of targeting or the mechanism of the effect thereof.

Finally, it is understood that the DNA can be derivatized to a variety of moieties which include, intercalators, chelators, lipophilic groups, label, or any other substituent which modifies but does not materially destroy the oligomeric character of the backbone.

C. Synthesis of the Analogs

The oligomers of the invention which contain the modified internucleoside linkages can be synthesized using reactions known in the art of oligonucleotide derivative synthesis. See e.g. Flandor, J. and Yam, S. Y., *Tet Letts* (1990) 31:597–600; Mattson, R. J. et al., *J Org Chem* (1990) 55:2552–2554; Chung, C. K. et al., *J Org Chem* (1989) 54:2767–2769.

Figure 2:
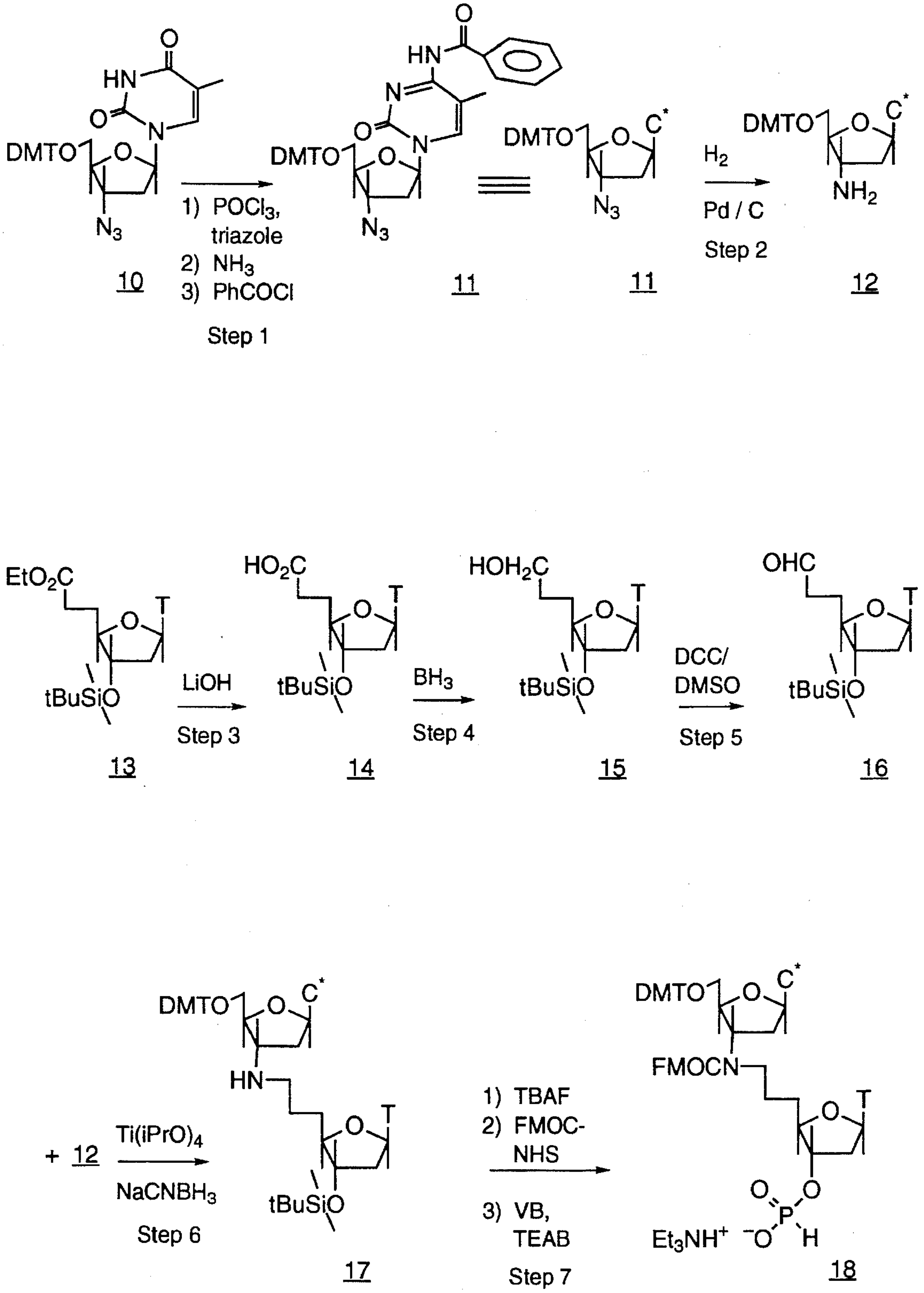
Figure 3:
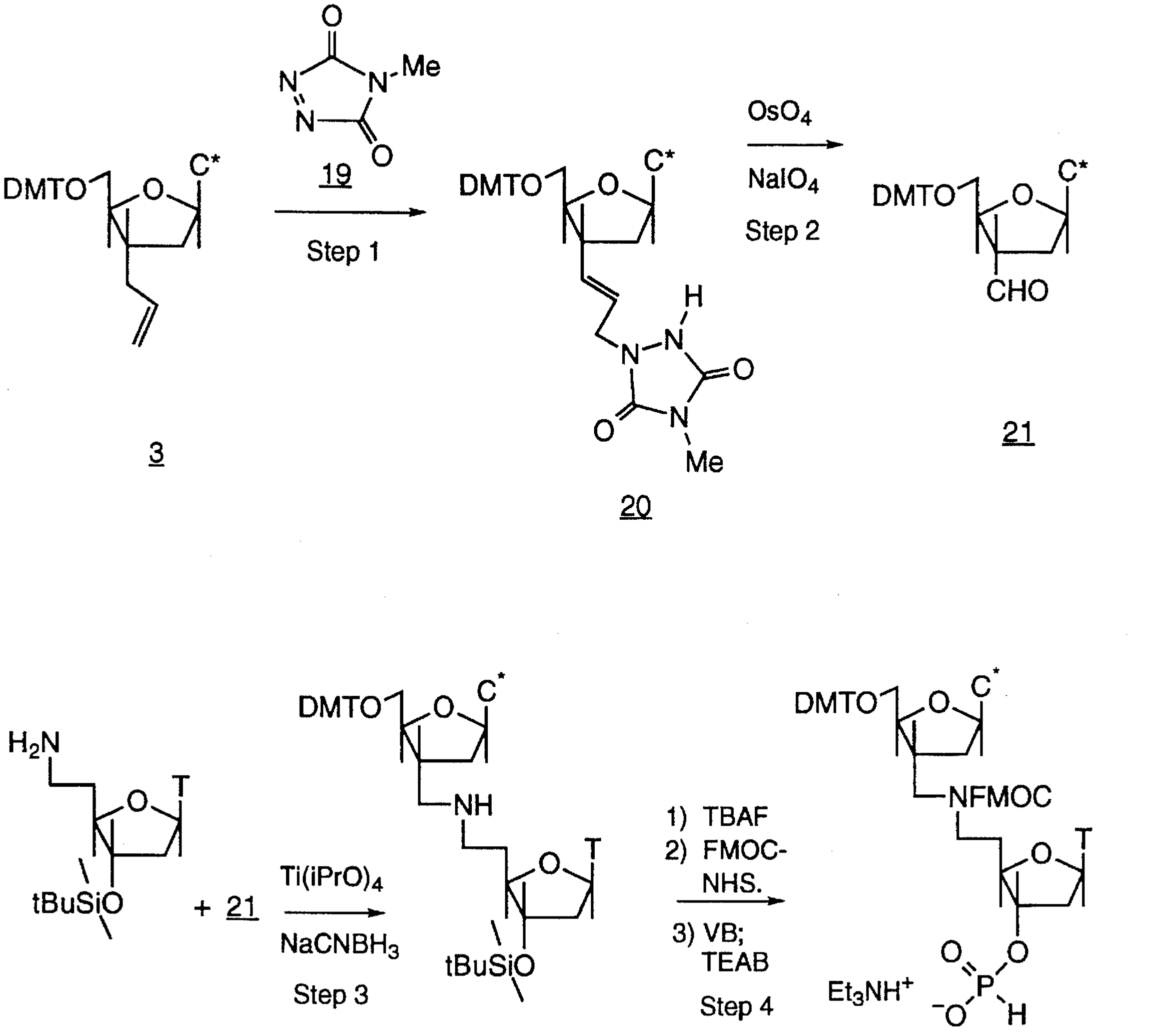
Figure 4:
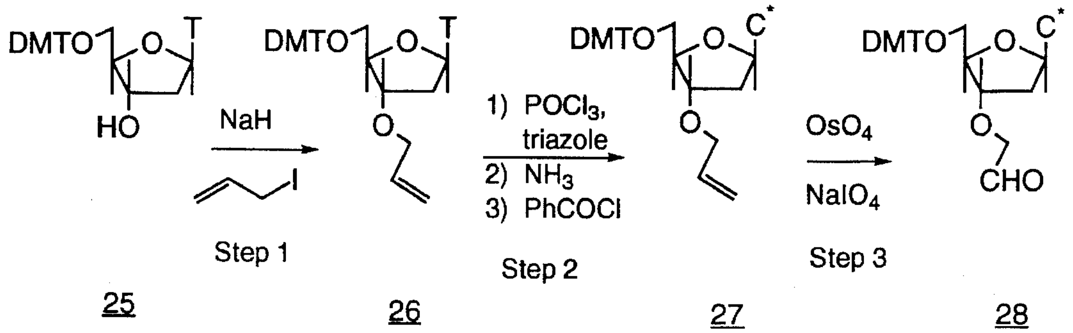
Figure 4:
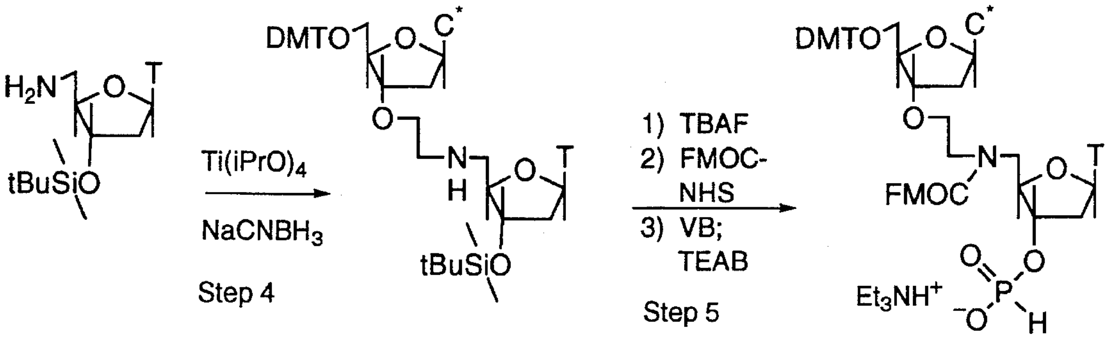
Figure 5:
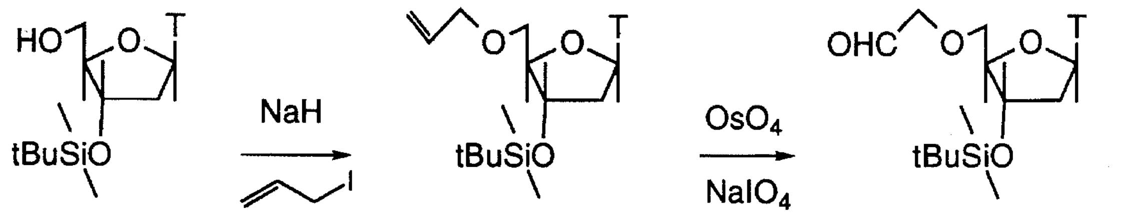
Figure 5:
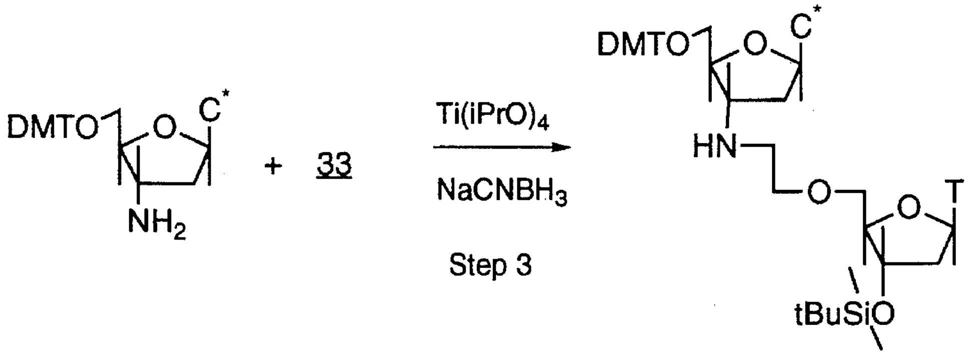
Figure 5:
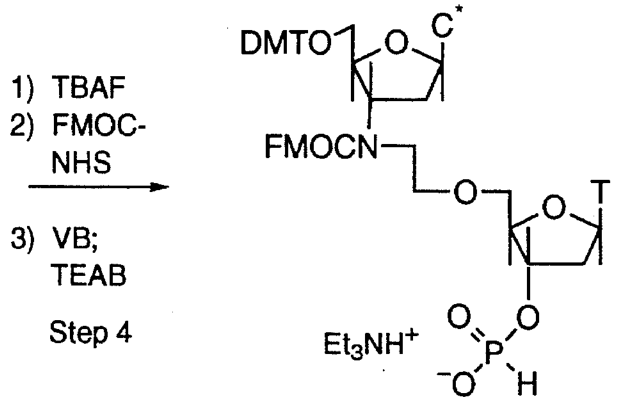
Figure 6:
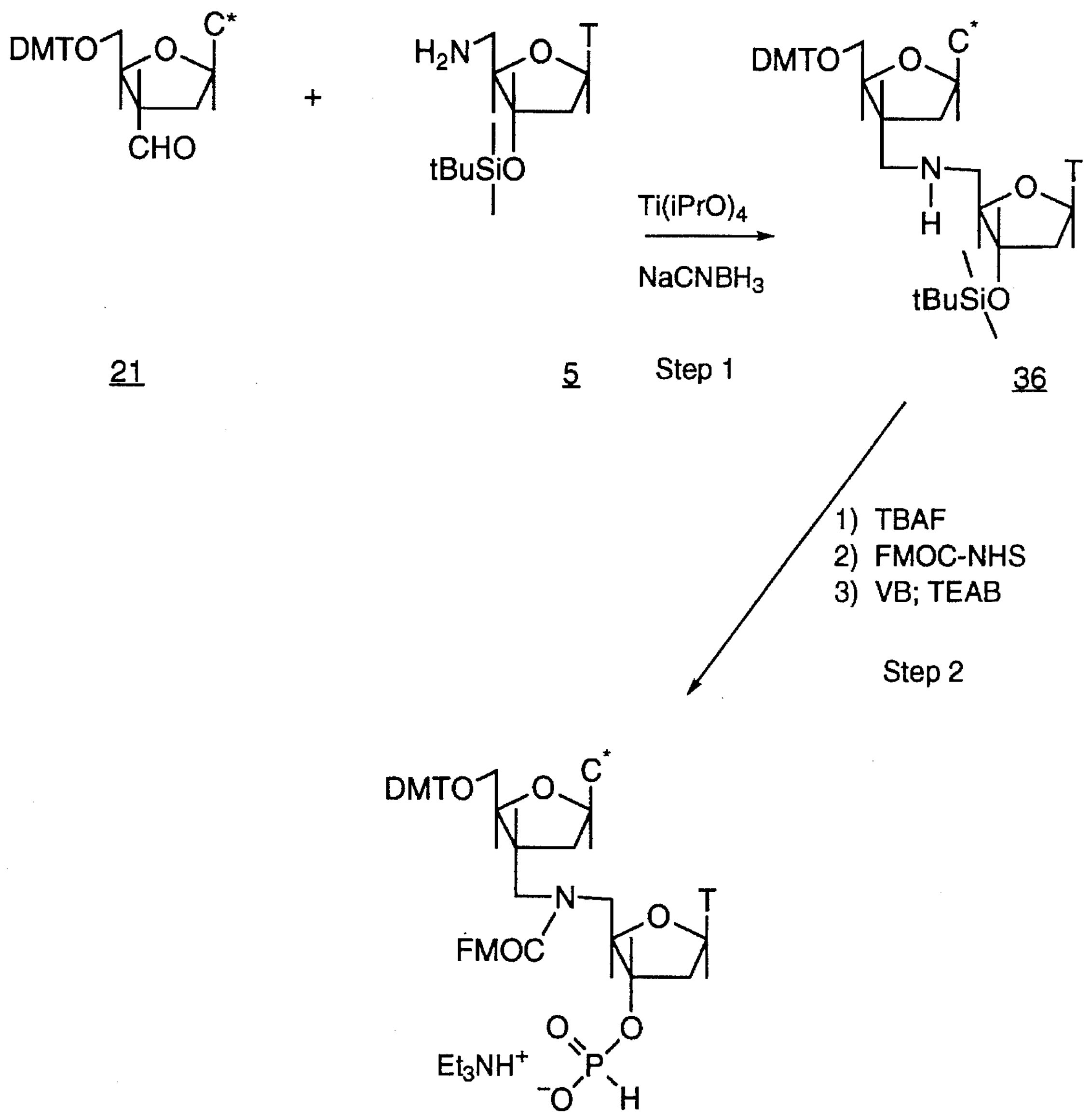
Figure 7:
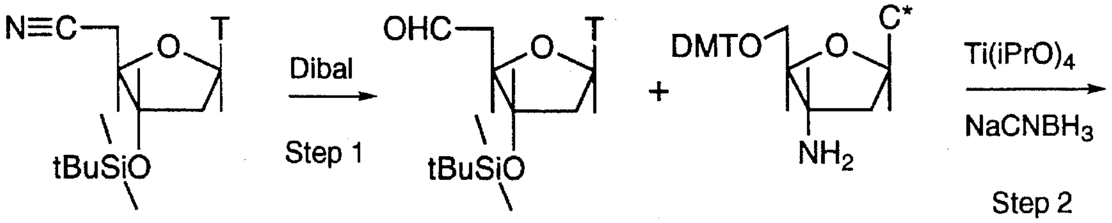
Figure 7:
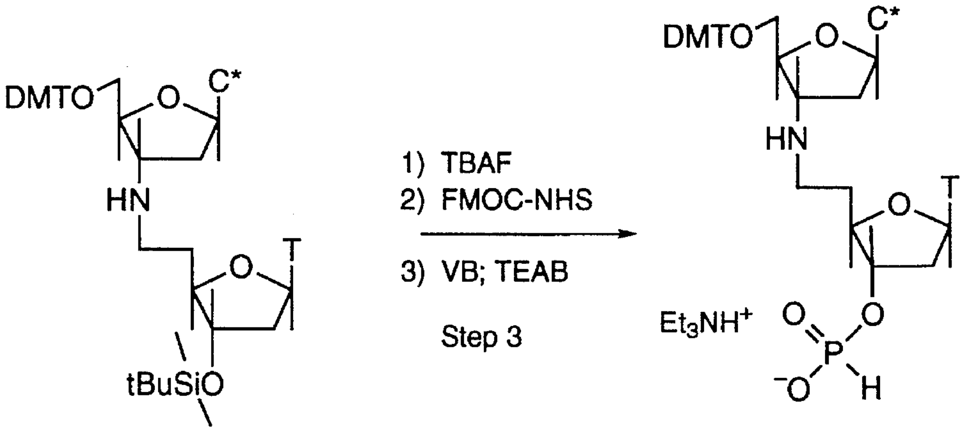
Figure 8:
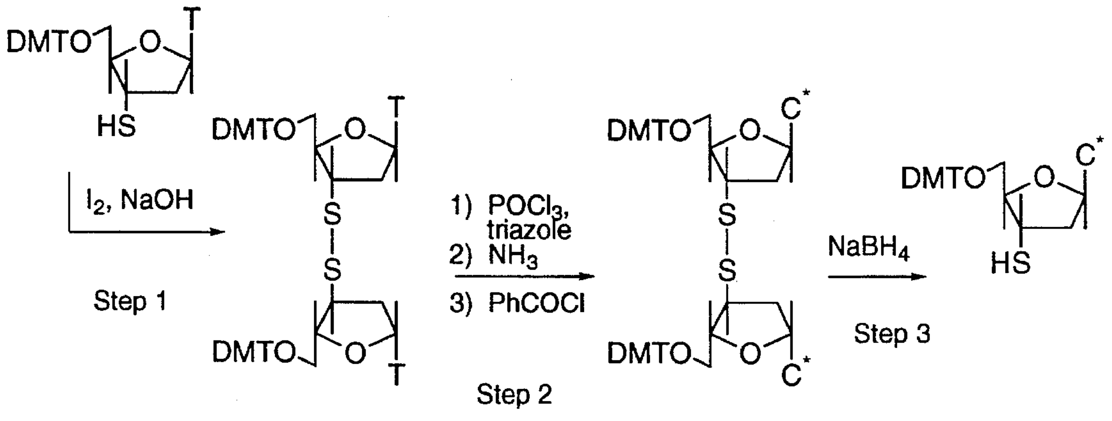
Figure 8:
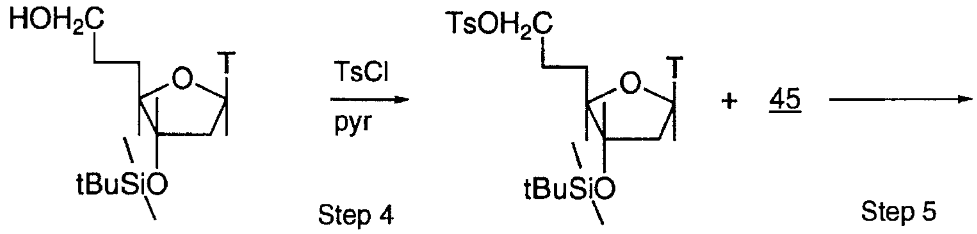
Figure 8:
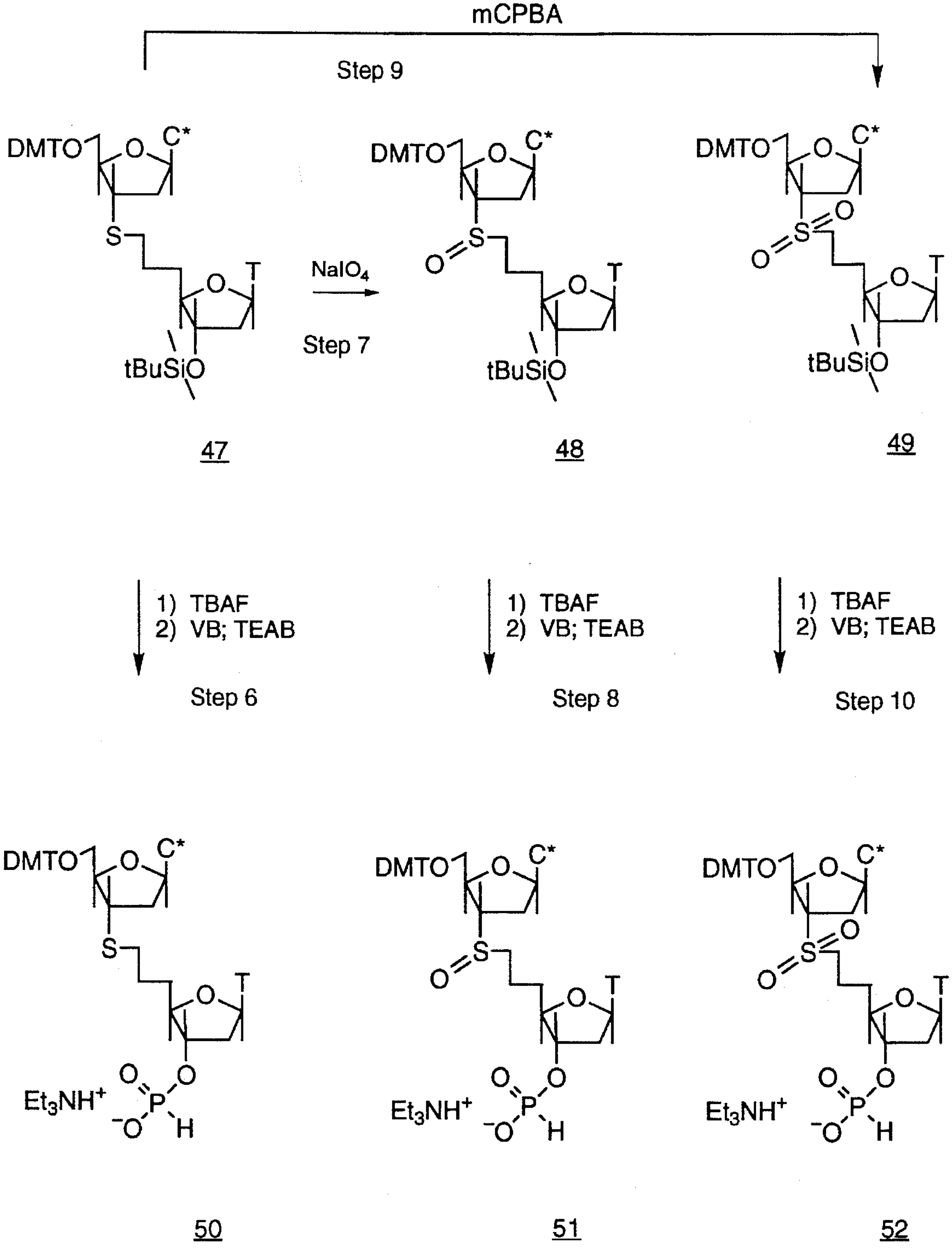
Figure 9:
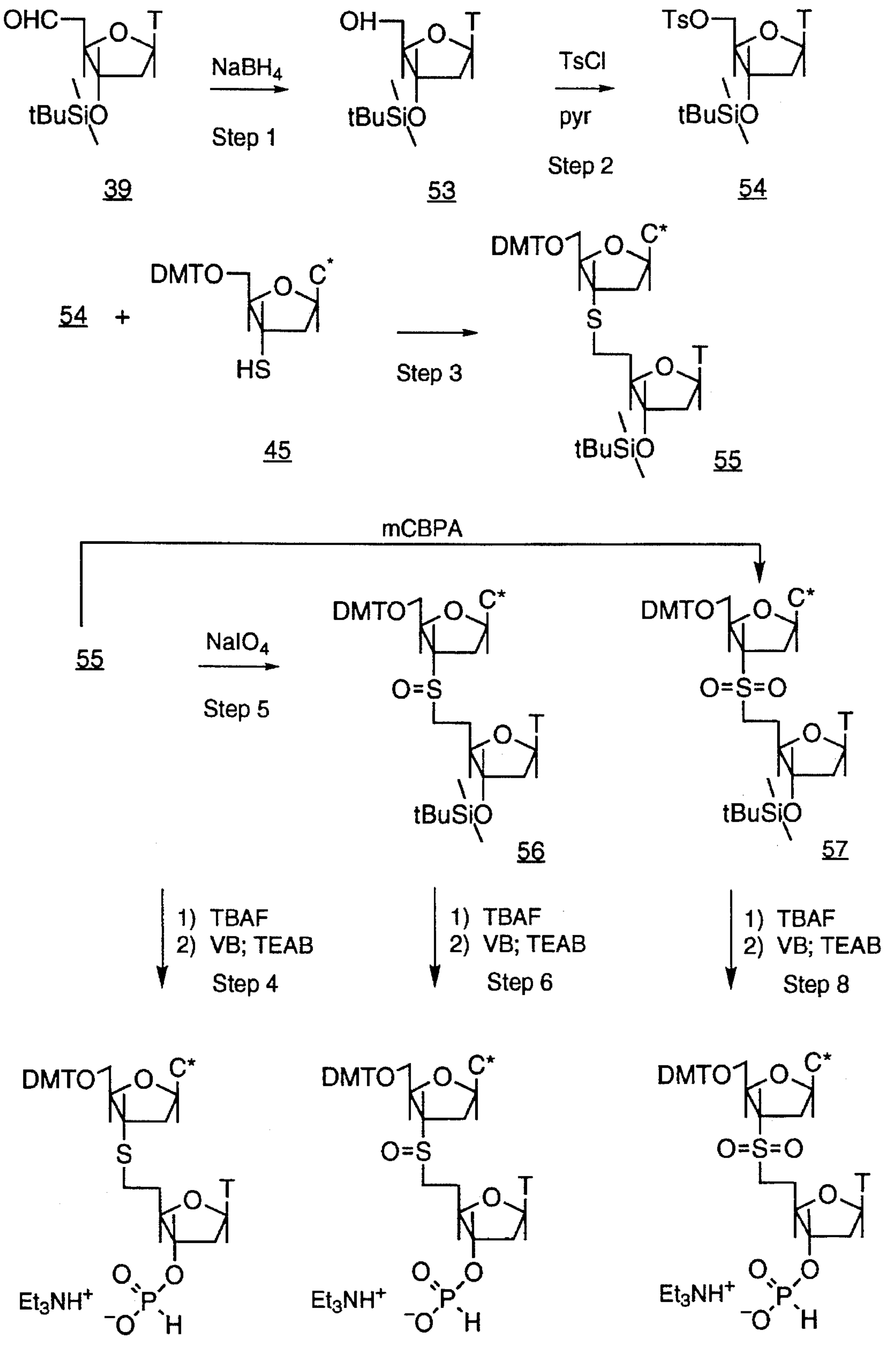
Figure 10:
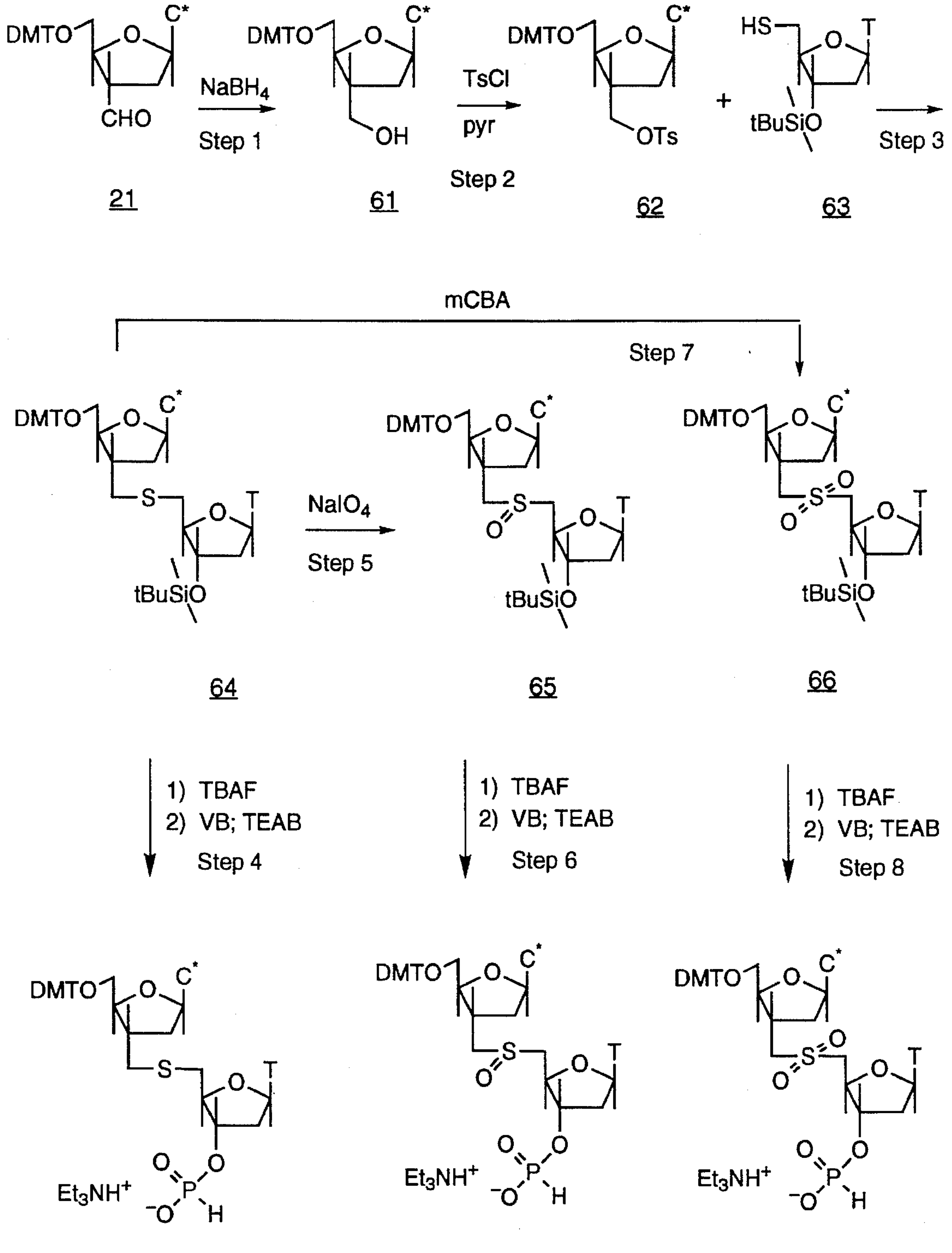
Figure 11:
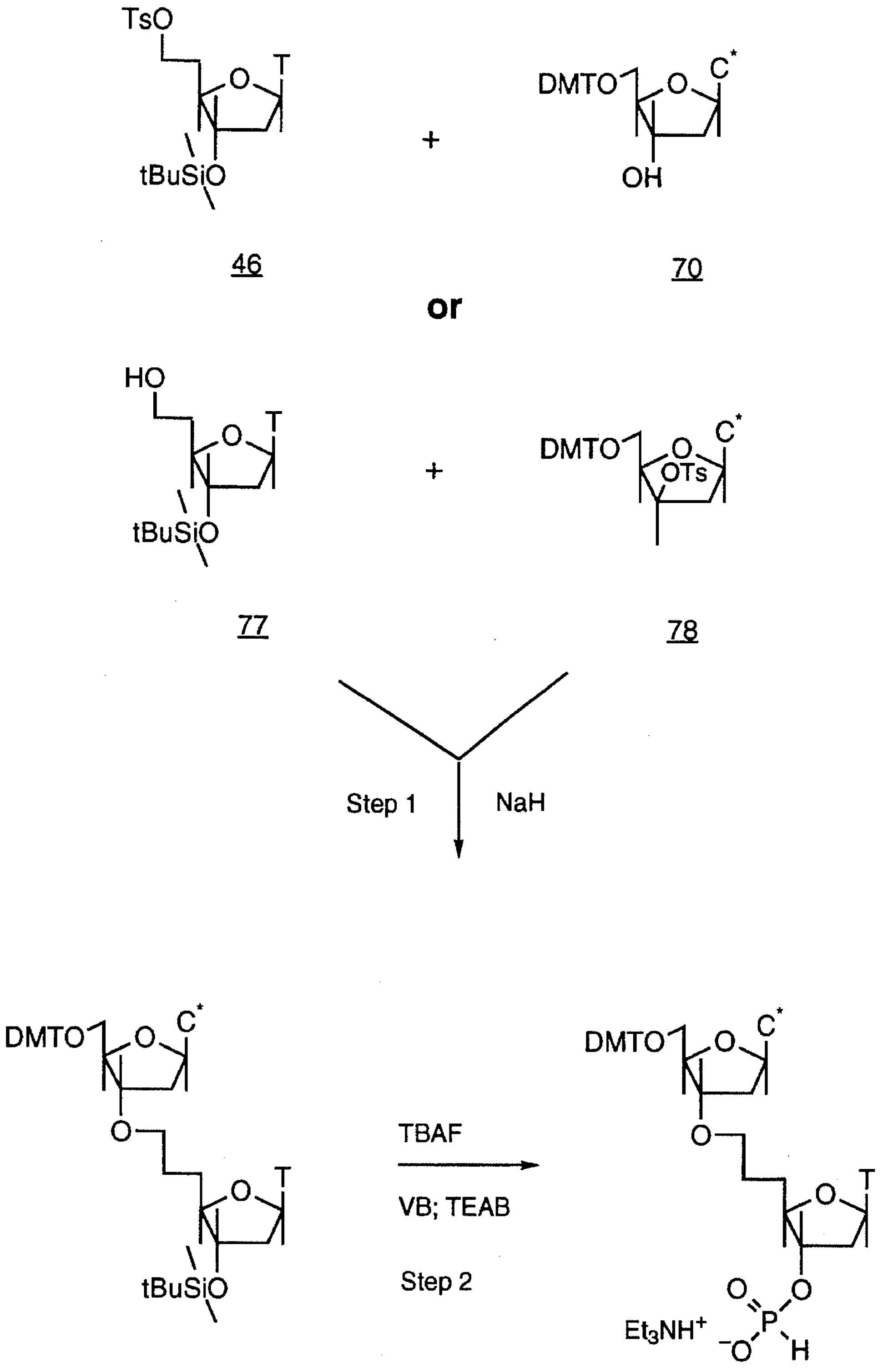
Figure 12:
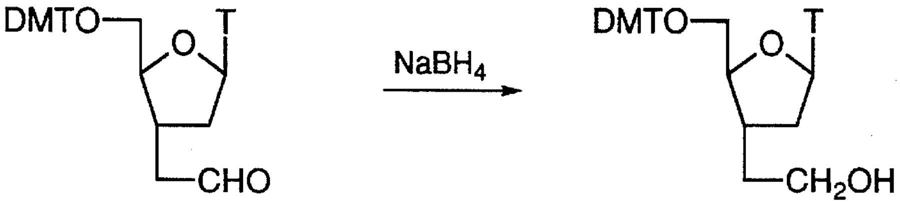
Figure 12:
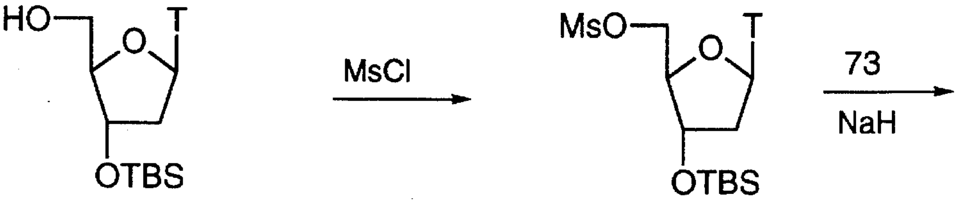
Figure 12:
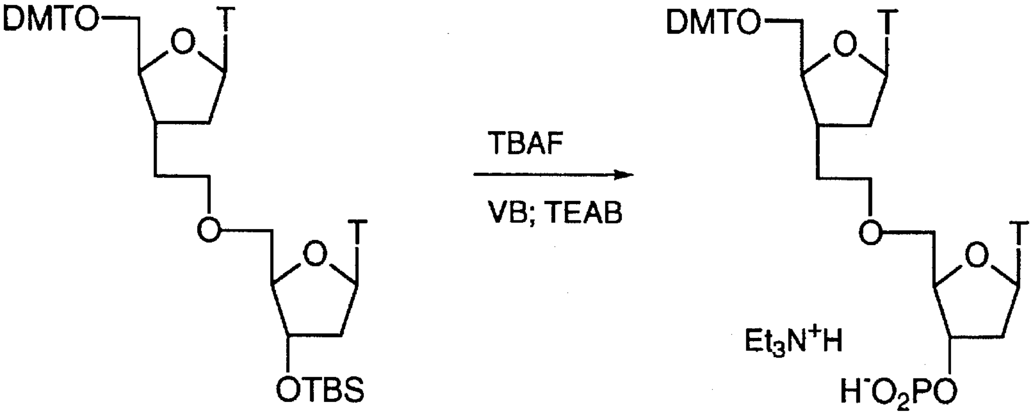
Figure 13:
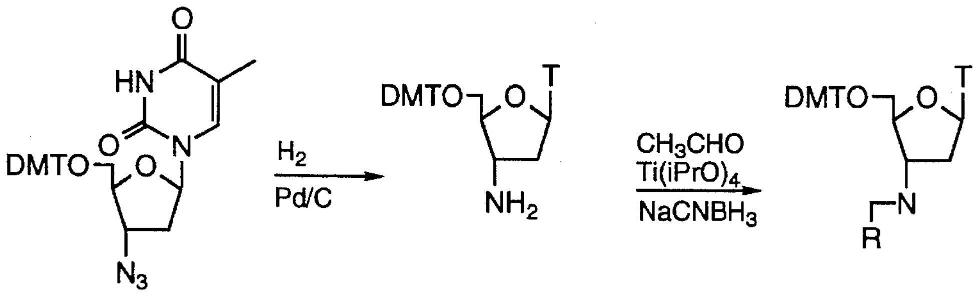
Figure 13:
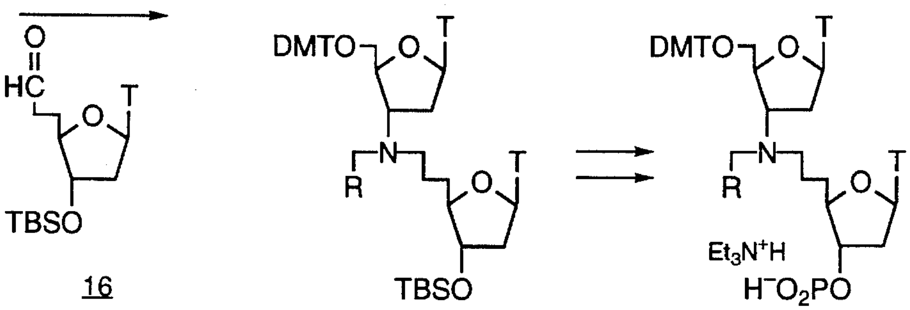
Figure 13:
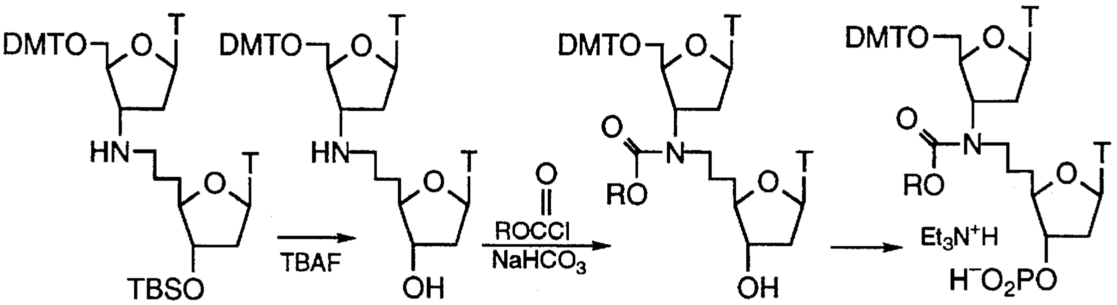
Figure 14:
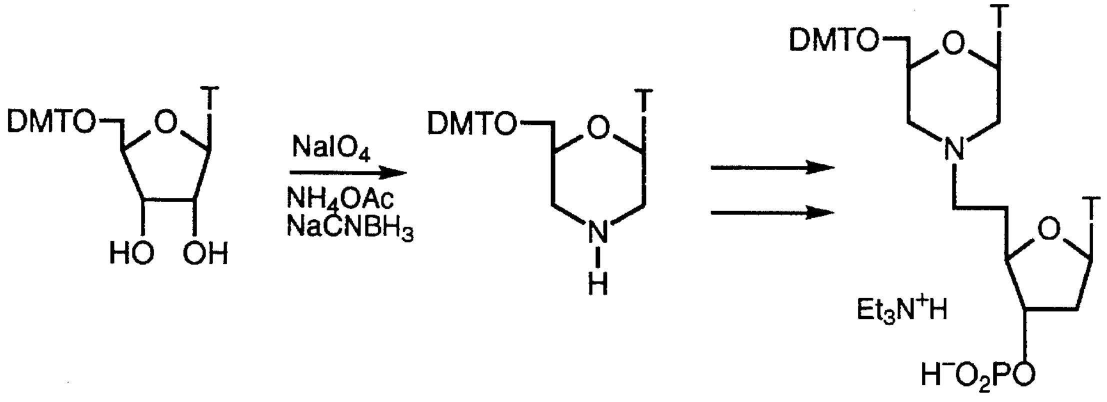
Figure 14:
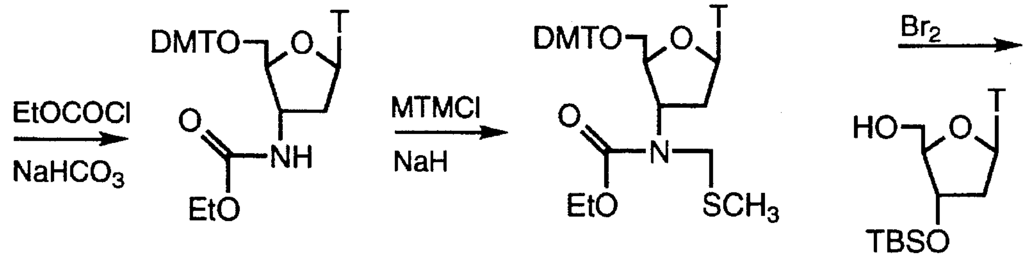
Figure 14:
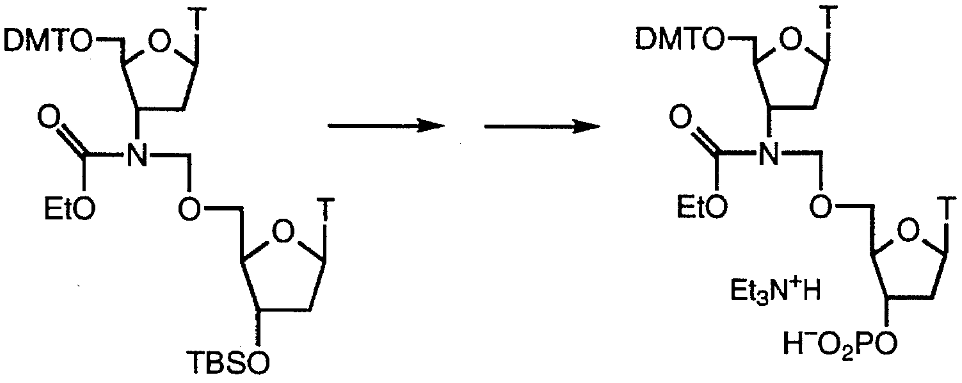

As can be seen from the variety of linkages specifically listed in Table 1, the linkages of the invention can vary so as to contain one or more nitrogen, sulfur, and/or oxygen atoms in their linking structure. The positions of these atoms in the linkage can vary from the "5'" end, to the "middle" to the "3'" end. In this section, a series of representative synthesis reaction schemes are set forth which provide routes to various locations and combinations of nitrogen, oxygen, and sulfur atoms within the linkages. Specifically, Scheme 1 shown in FIG. 1, shows the formation of a nucleotide dimer containing a three atom long linkage with a nitrogen at the 5' end of the 3' nucleoside. Scheme 2, depicted in FIG. 2, shows the formation of a three atom long linkage with a nitrogen at the 3' end of the 5' nucleoside. Scheme 3, shown in FIG. 3, depicts the formation of a three atom long linkage with a nitrogen in the middle. Scheme 4, shown in FIG. 4, depicts the formation of a four atom long linkage with oxygen at the 3' end and nitrogen at the 5' end. Scheme 5, depicted in FIG. 5, shows the formation of a four atom long linkage with nitrogen at the 3' end and oxygen at the 5' end. Scheme 6, shown in FIG. 6, depicts the formation of a two atom long linkage with nitrogen at the. 5' end. Scheme 7, depicted in FIG. 7, shows the formation of a two atom long linkage with nitrogen at the 3' end. Scheme 8, represented in FIG. 8, shows the formation of three different three atom long linkages with sulfur at the 3' end. Scheme 9, represented in FIG. 9, depicts the formation of three different two atom long linkages with sulfur at the 3' end. Scheme 10, depicted in FIG. 10, shows the formation of three different two atom long linkages with sulfur at the 5' end. Scheme 11, shown in FIG. 11, depicts the formation of a three atom long linkage with oxygen at the 3' end. Scheme 12 as shown in FIG. 12 depicts the formation of a three atom long linkage with oxygen at the 5' end. Scheme 13, depicted in FIG. 13, shows the formation of alkyl derivatives of a three atom long linkage with nitrogen at the 3' end. Scheme 14, shown in FIG. 14, shows the formation of a three atom long morpholino derivative. Finally, Scheme 5, depicted in FIG. 15, demonstrates the preparation of a three atom long linkage with sulfur at the 3' end. These schemes can be modified as is known to those practicing in the area of oligonucleotide chemistry. For example, although protection of the bases is not always indicated in the synthesis schemes, such may be desireable and can be accomplished using reagents and techniques known in the art. See, e.g. *Protective Groups in Organic Synthesis* (Theodora W. Greene, John Wiley and Sons, 1981). Similarly, although the use of protective groups is shown in some cases, it is not always necessary to block the reactants in order to synthesize the exemplified modified oligomers.

Turning to FIG. 1, the first two steps shown in Scheme 1 relate to the derivatization of thymine to a protected cytosine. The third and subsequent steps in Scheme 1 are directed to the synthesis of modified backbone materials. The starting materials such as the material shown as compound 1 in Scheme 1 are 3'-deoxy-3'-2-allyl nucleosides. These allyl materials are analogous to the 3'-deoxy-3'-2-propanyl thymidyl derivatives described in Flandor, J. and Yam, S. Y., supra.

In step 1 of Scheme 1, the reactive 5'-hydroxyl in the nucleoside sugar is reacted with dimethoxytritylchloride (DMTCl) to protect it and yields compound 2. Other equivalent protecting groups may be used. In the next step, the carboxyl oxygen at the 4-position of compound 2 is converted to an amine to yield cytosine. The amine is in turn coupled to a benzoyl group. This is typically carried out in three substeps by first reacting the 4' carboxyl with $POCl_3$ in the presence of a triethyl amine and triazole. The product of that reaction is recovered and treated with ammonia gas at low temperature to form an amine group. This product is recovered and the newly added amine reacted with a suitable protecting group such as benzoyl chloride or FMOC NHS ester. This yields the material shown as compound 3 in Scheme 1. For simplicity, compound 3 and its protected cytosine residue are abbreviated as shown. The 3'-allyl group of compound 3 is then oxidized such as with $OsO_4$/$NaIO_4$ to yield the aldehyde intermediate 4. The aldehyde 4 is then reacted with a 5-deoxy,5'-amino, 3'-protected nucleoside, which can be selected from a range of known compounds and the resulting imine is reduced. This reductive alkylation reaction can be advantageously carried out using a suitable catalyst such as titanium isopropoxide and cyanoborohydride (see Mattson, R. J. et al., supra). This yields a pair of protected nucleosides joined through a $—CH_2—CH_2—NH—$ modified internucleoside linkage. Compound 6 in Scheme 1 is representative.

Thereafter, the 3'-hydroxyl protecting group is removed to yield compound 7. The amine group in the internucleoside linkage is protected, such as with an FMOC group to yield compound 8 and a phosphonate group is added to the 3'-hydroxyl with Van Boom's reagent (VB). This yields dimer 9 which has two nucleosides joined through a $—CH_2—CH_2—NH—$ modified internucleoside linkage, a free 3'-phosphonate group and a blocked 5'-position. This dimer can then be added into a growing oligonucleotide using conventional chemistry. Alternatively, the resulting dimer or oligomer may be succinylated as a convenient linker for coupling to a solid support, such as controlled pore glass (CPG). The coupled modified oligomer can be used as a starting material for standard oligonucleotide synthesis, as, for example, using H-phosphonate chemistry as described by Froehler, B., et al., *Nucleic Acids Res* (1986) 14:5399. This synthesis involves deprotection of the 5'-hydroxyl using dichloroacetic acid in methylene chloride and treatment with a 5'-DMT-protected base 3'-phosphonate in the presence of acetyl chloride/pyrimidine/acetonitrile, and repetition of this deprotection and linkage protocol for any desired number of times.

Alternatively, the liberated 3'—OH can be linked via an ester linkage to a solid support analogous to standard oligonucleotide synthesis (Matteucci, M. et al., *J Am Chem Soc* (1981) 103:3185, for extension of oligonucleotide. The final product is removed from the solid support by standard procedures, such as treatment with iodine in a basic aqueous medium containing THF or other inert solvent, followed by treatment with ammonium hydroxide. Deprotection of the nucleotide bases attached to the added nucleotides is also conducted by standard procedures. Similarly, the FMOC group protecting the nitrogen present in the internucleoside linker can be removed conventionally and, if desired, replaced by other R groups as set forth herein.

The modified internucleoside linkage can be included at any arbitrary position in an oligonucleotide by substituting for a conventional monomer in the sequential synthesis, a protected dimer containing the modified linkage which has been synthesized, for example, by the steps set forth in Scheme 1 shown in FIG. 1.

Any DNA synthesis chemistry such as phosphoramidate or phosphonate chemistry can be used to link monomers or dimers in a manner analogous to that set forth above.

Turning to FIG. 2, a representative route (Scheme 2) is provided for generating a three atom long linkage with a nitrogen at the 3' position is shown. In the Scheme, Step 1 concerns the formation of a 5-methylcytosine derivative 11 having an $N_3$ group at its 3' position. In Step 2 this $N_3$ group is reduced to an amine such as with hydrogen and a hydrogenitive catalyst to yield compound 12: Step 3 begins with a known ester compound 13 (U.S. Pat. No. 4,882,316 (1989) and *J. Org. Chem.* (1981) 46;594). This material is treated with base to hydrolyze the ester, and treated with acid to yield the free acid 14. The acid is then selectively reduced to the alcohol 15 using for example a borane reducing agent. The alcohol 15 is converted to the aldehyde 16 such as by using a carbodiimide. Aldehyde 16 and amine 12 are then coupled in Step 6 and converted to phosphonate 18 in a manner analogous to that used in Scheme 1 by treatment with TBAF (Tetrabutyl ammonium fluoride), FMOC-NHS and Van Boom's reagent plus TEAB.

In Reaction Scheme 3 (shown in FIG. 3) the starting material is a 3'-alkyl substituted protected nucleoside such as 3. In Step 1 the alkyl double bond is displaced by coupling the alkyl group to 19. Step 2, which is analogous to Step 3 in Scheme 1, can be used to generate a 3'-aldehyde substituent present in compound 21. This aldehyde can then be coupled to the known amine 22 in Step 3 and converted to the phosphonate in Step 4 which are analogous to the steps fully described in Schemes 1 and 2.

In FIG. 4 a route for producing an oxygen- and nitrogen-containing linkage is given. A free 3' hydroxyl is reacted in Step 1 with allyl iodide in the presence of sodium hydride to couple the allyl group to the free hydroxyl and yield compound 26. Step 2 in Scheme 4 involves a three-substep process for converting the thymidine analog present as 26 to a protected cytosine 27. As in Scheme 1, the allyl group in 27 is then oxidized to an aldehyde 28 which is reacted with amine-substituted nucleoside derivative 5 in Step 4 to give the two nucleosides coupled through a linkage of the invention and yield "dimer 29" which is converted to the phosphonate form 30 using the methodology set out in Scheme 1.

Scheme 5, shown in FIG. 5, is essentially the "reverse" of Scheme 4 in that the nitrogen is placed in the 3' position and the oxygen in the 5' position. Essentially the same reactions are conducted using different blocking and substitution patterns to achieve the reverse orientation.

Scheme 6, shown in FIG. 6, provides a two atom long linkage. It employs as representative nucleoside analog starting materials, aldehyde 21 (produced in Scheme 3) and amine 5 (noted as available in Scheme 1). These materials are coupled and converted to a phosphonate in Steps 1 and 2 which are analogous to Steps 6 and 7 of Scheme 2.

Scheme 7 shown in FIG. 7 also involves a 2 atom linkage, this time with a nitrogen at the "5'" end. This reaction sequence starts with the known 5' nitrile 38 which is converted to an aldehyde 39 in Step 1. This aldehyde then is coupled to amine 12 (previously prepared) in Step 2 and converted to a phosphonate in Step 3, again analogous to Steps 6 and 7 of Scheme 2.

Scheme 8, shown in FIG. 8, provides a route to three atom long linkers containing materials having sulfur in various oxidation states at the 3' end of the linkage. The scheme begins with the known thiol 42. Steps 1, 2 and 3 all relate to forming a cytosine analog 45 from this thymidine analog 42. In Step 4 the alcohol group on compound 15 (produced in Scheme 2) is reacted with losyl chloride. Tosylate 46 is then coupled with thiol 45 in Step 5 to yield sulfur-containing "dimer" 47. Dimer 47, having sulfur as —S— can be converted directly to a phosphonate as shown in Step 6. Alternatively the sulfur can be partially oxidized with $NaIO_4$ (Step 7) to

—S—
||
O or with an CPPBA (Step 9) to

O
||
—S—
||
O and then converted to the respective phosphonates as shown in Steps 8 and 10.

In Scheme 9 a two atom long sulfur containing linkage is constructed. Aldehyde 39, prepared in Scheme 7 is reduced to alcohol 53 with a borohydride reducing agent. The alcohol is converted to a tosylate 54 which is then coupled to the thiol 45 from Scheme 8 in Step 3 to yield "dimer" 55.

Dimer 55 is then converted to the phosphonate with or without oxidation in Steps 4, 5–6 and 7–8 respectively.

FIG. 10 shows Scheme 10 which is directly analogous to Schemes 8 and 9 just described with variation in the position of the aldehyde group and thiol group. Again, this scheme gives rise to 3 families of materials 67, 68 and 69 which differ from one another in terms of sulfur oxidation state.

Schemes 11 and 12 are representative routes to materials linked with oxygen present at the 3' and 5' ends of the linking group.

In Scheme 11, two routes are shown. In one a "5'" tosylate 46 is reacted with a "3'" alcohol 70 to yield dimer 71 which is converted to a phosphonate to yield 72. Alternatively a 3' tosylate 78 can be reacted with a 5' alcohol 77 to yield 71.

In Scheme 12, 3' aldehyde 4 is reduced to 3' alcohol 74 which is coupled to 5' tosylate 73 to give oxygen-containing linked material 75 which is converted to phosphonate 76 or alternatively a 3' tosylate 80 is reacted with a 5' alcohol to give the same product.

FIG. 13, Scheme 13, shows the synthesis of alkyl derivatives of a 3' amine of a three atom long linkage. Azide 10 is hydrogenated to deliver the amine 80. Amines 81, 82 and 83 are treated with acetaldehyde toluene, and titanium isopropoxide and the products coupled with aldehyde 16, as described for amine 12, to yield dimers 84–86 which are in turn converted to the corresponding phosphonates 87–89, as described for compound 18. Acylated derivatives of the 3' amine begin with dimer 90, which is prepared as explained for compound 17. The products are ultimately converted to phosphonates as described further below.

The synthesis of a morpholino-containing linkage (FIG. 14, Scheme 14) begins with a protected 5'methyluridine 96. The resulting morpholine, 97, is reacted with aldehyde to form a dimer, and subsequently converted to a phosphonate, 98, as described for compound 18. The aminal derivative is prepared from amine acylated to yield carbamate 99, which is alkylated to produce thioaminal 100 which is ultimately converted to the corresponding phosphonate.

Figure 15:
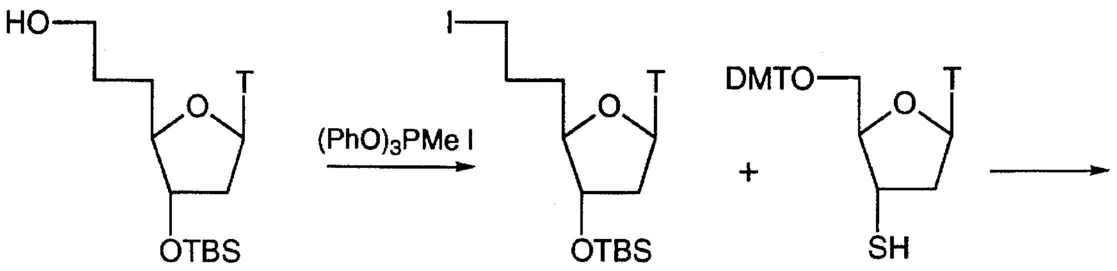
Figure 15:
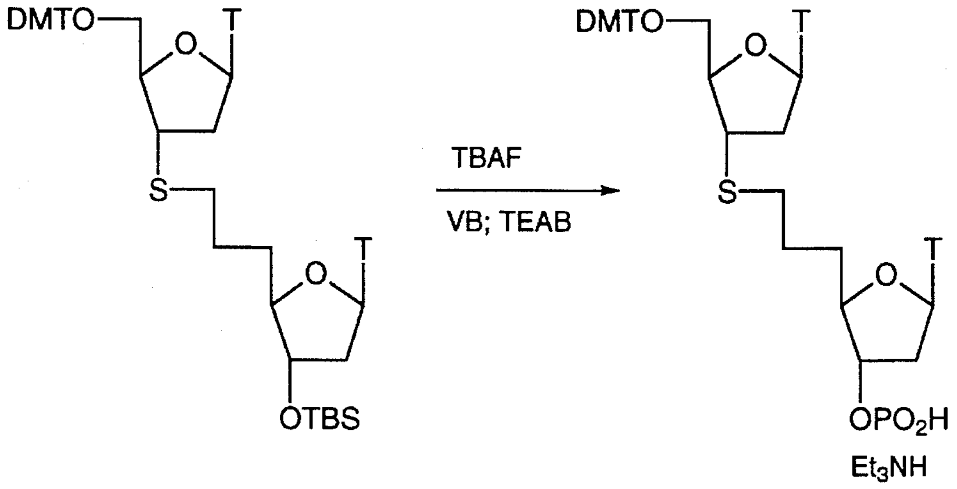

FIG. 15, Scheme 15, shows the preparation of a three atom long linkage with a 3' sulfur. Alcohol 42 in DMF and pyridine is reacted within methyltriphenoxyphosphonium iodide. The product is saturated with sodium thiosulfate to yield iodide 103. Thiol 42 and acetonitrile are combined with acetamide and DMF, and iodide added, to ultimately yield dimer 104 which is converted to a phosphorate as described for compound 18.

The following examples are intended to illustrate but not to limit the invention.

D. Experimental

EXAMPLE 1

Preparation of Cme($CH_2$—$CH_2$—NR)T

The compounds used and generated in this example are shown in Scheme 1, shown in FIG. 1.

To a flask containing compound 1 (2.21 g, 8.30 mmol) (Flandor, J. and Yam, S. Y., *Tet Letts* (1990) 31:597–600; *J Org Chem* (1989) 54:2767–2769) was added pyridine (25 ml) and the solution was evaporated to dryness. Pyridine (25 ml) was added again followed by DMT-Cl (3.67 g, 10.34 mmol); the solution was stirred for 18 hours and poured in 10% aq sodium bicarbonate solution. The crude product was extracted with $CHCl_3$ (3×50 ml), dried ($Na_2SO_4$), stripped to dryness, and chromatographed on silica gel (5% MeOH/MC) (methylene chloride) to yield the product 2 (4.20 g).

To a solution of compound 2 (1.60 g, 2.81 mmol), $Et_3N$ (7.8 ml, 56 mmol), 1,2,4 triazole (3.88 g, 56 mmol) and acetonitrile (75 ml) at 0° C. was added $POCl_3$ (0.49 ml, 4.2 mmol) dropwise over ½ hours. The mixture was poured into water (150 ml) and the crude product was extracted with chloroform (3×100 ml), dried ($Na_2SO_4$) and concentrated. The residue was dissolved in acetonitrile (75 ml) and cooled 0° C. Ammonia gas was bubbled through the solution for 15 minutes, and the solution was allowed to warm to ambient temperature and stirred for 18 hours. The reaction mixture was poured into 10% aq sodium bicarbonate, and the crude product was extracted with chloroform (3×100 ml), dried $Na_2SO_4$) and concentrated. The concentrate was dissolved in pyridine (75 ml) and cooled to 0° C. Benzoyl chloride (0.49 ml, 4.2 mmol) was added dropwise over 10 minutes. 10% Aqueous sodium bicarbonate (100 ml) was added and the solution was stirred for 30 minutes. The crude product was extracted with chloroform (3×75 ml); dried ($Na_2SO_4$); and concentrated to dryness. Toluene (200 ml) was added and the solution was again concentrated to dryness. Silica gel chromatography (1% $Et_3N$/5 to 10% MeOH/MC) afforded 3 (1.65 g).

To a solution of 3 (672 mg, 1 mmol) in dioxane (25 ml) and 1% aqueous sodium bicarbonate (20 ml) was added osmium tetroxide (0.5 ml, 2.5 wt % solution in t-butyl alcohol), and the solution stirred for 5 minutes. Sodium periodate (2.9 g, 15 mmol) was added in four portions, and the mixture was stirred for 18 hours. The solution was poured into 10% aqueous saturated bicarbonate (100 ml) and the crude product was extracted with chloroform (3×15 ml); dried ($Na_2SO_4$); and concentrated. The resulting oil was taken up in methylene chloride (50 ml); filtered through celite and concentrated (310 mg). To this aldehyde was added, 5'-amino, 3-(O-t butyldimethylsilyl)thymidine (180 mg, 5.1 mmole), toluene (15 ml), and titanium tetraisopropoxide (0.275 ml, 0.92 mmole). After stirring for 1 hours, abs. ethanol (20 ml) and sodium cyanoborohydride (10 mg, 1.5 mmol) were added and the reaction was stirred for 18 hours. The solution was poured into 10% aq sodium bicarbonate solution (50 mL) and the crude product was extracted with chloroform (3×50 ml); dried ($Na_2SO_4$); stripped to dryness, and chromatographed on silica (1% $Et_3N$/5 to 10% methanol/MC) to yield the product 6 (230 mg). (See *J Org Chem* (1990) 55:2552–2554).

Compound 6 (227 gm, 0.22 mmol) was dissolved in THF (20 ml) and tetrabutylammonium fluoride (1.0M in THF, 0.5 ml) was added. The reaction solution was stirred for 2 hours, concentrated and applied to a silica gel column and chromatographed (1% $Et_3N$/5 to 10 to 15% MeOH/MC) to yield the product 7 (174 mg).

To a solution of compound 7 (160 mg, 0.17 mmol) in acetonitrile (5 ml) and methanol (5 ml) was added N(9-Fluorenylmethoxycarbonyloxy) succinimide (100 mg, XS), and the solution was stirred for 15 minutes. The crude product was concentrated to dryness; toluene (50 ml) was then added and the solution was again evaporated to dryness to deliver the product 8 (200 mg).

Compound 8 (200 mg, 1.8 mmol) was dried by azeotropic distillation with pyridine (2×50 ml). To a solution of 8 in pyridine (2 ml) and MC (2 ml) at 0° C. was added a solution of 2-chloro-4H-1,3,2-benzodioxaphosphorin-4-one (1 M in MC, 0.5 ml, 0.5 mmol). The solution was stirred for 45 minutes and quenched with pH 7.5 triethyl ammonium bicarbonate (TEAB) (1M, 10 ml). The crude product was extracted with 4:1 MC/n-butanol (3×25 ml), dried ($Na_2SO_4$), and diluted with 50 ml of acetonitrile. The solution was concentrated and chromatographed on silica gel (1% pyr/O to 20% $H_2O$/acetonitrile). The product-containing fractions were concentrated, diluted with toluene and concentrated again. The product was then dissolved in 3:1 MC/n-butanol and back extracted with pH 7.5 triethylammonium bicarbonate. The organic layer was dried ($Na_2SO_4$), diluted with acetonitrile (50 ml), and concentrated to afford the final product 9 (125 mg). The FMOC group can be substituted using conventional techniques.

EXAMPLE 2

Preparation of Cme(NR—$CH_2$—$CH_2$) T

The compounds used and generated in this example are shown in Scheme 2, FIG. 2. Compound 10 was converted to the 5-methyl cytosine (Cme—C*) derivative 11 in an analogous fashion to that described for compound 2 (Example 1). A mixture of compound 11 (2.00 g, 2.90 mmol), 10% palladium on carbon (200 mg), ethyl acetate (20 ml), and methanol (200 ml) was hydrogenated at atmospheric pressure for 6 hours. The reaction mixture was filtered through celite, and the solvent was evaporated. The crude product was chromatographed on silica gel (0.5% TEA/5% MeOH/MC) to yield the product 12 (1.30 g).

Compound 13 (4.26 g, 10 mmol) (U.S. Pat. No. 4,882, 316; Montgomery, J. A. and Thomas, H. J., *J Org Chem* (1981) 46:594) was dissolved in dioxane (30 ml) and water (10 ml) and treated with lithium hydroxide (426 mg) for 2 hours. The solution was poured into ice cold 0.1M $H_3PO_4$ (100 ml) and chloroform (100 ml). The crude product was extracted with chloroform (2×50 ml), dried over $Na_2SO_4$, concentrated, and chromatographed on silica gel (5% methanol/MC) to yield the carboxylic acid 14 (3.26 g).

To a solution of carboxylic acid 14 (1.10 g, 2.76 mmol) in tetrahydrofuran (50 ml) at 0° C. was added $BH_3$—THF (30 ml, 1.0M in THF) in three portions. The mixture was slowly poured into ice cold aqueous sodium bicarbonate (100 ml). The product was extracted with chloroform (3×50 ml), dried over sodium sulfate, and concentrated to provide alcohol 15 (1.04 g).

A solution of 15 (1.04 g, 2.70 mmol) in DMSO (20 ml) was treated with NN'dicyclohexyl carbodiimide (DCC, 1.74 g) and dichloroacetic acid (100 μl), and the mixture was stirred for 18 hours. The reaction mixture was poured into 5% aqueous bicarbonate, and the crude product was extracted with chloroform (3×50 ml), dried over sodium sulfate, concentrated, and chromatographed on silica gel (5% MeOH/MC) to afford the aldehyde 16 (403 mg).

The aldehyde 16 and amine 12 were coupled and then converted into the phosphonate 18 in analogous fashion as described for compound 6 (Example 1). Following synthesis, the FMOC group can be replaced using conventional methods.

EXAMPLE 3

Preparation of Cme($CH_2$—NR—$CH_2$)T

The compounds used and generated in this example are shown in Scheme 3, FIG. 3.

Preparation of 20: To a dry (azeotroped from pyridine at reduced pressure) sample of compound 3 (0.20 g, 0.35 mmol) was added dry $CHCl_3$ (2.0 mL, ethanol-free) and stirred at room temperature until a solution resulted. To this solution was added 4-methyl-1,2,4-triazoline-3,5-dione (0.06 g, 0.53 mmol, Aldrich Chemical Co., Inc.). The resulting red solution was protected from light and allowed to stir at room temperature overnight. Analysis of the pale yellow solution indicated a large percentage of unreacted material. More 4-methyl-1,2,4-triazoline-3,5-dione (0.08 g, 0.71 mmol) was added, and the reaction mixture was protected from the light and allowed to stir at room temperature overnight. The reaction mixture was diluted with $CHCl_3$ (100 mL) and the organic phase washed with saturated aqueous $NaHCO_3$, separated, and dried over $Na_2SO_4$. Removal of solvents afforded a dark yellow oil, which was purified by column chromatography (Baker, Inc. silica gel, −40 μM particle size) using a step gradient of 4%–20% isopropyl alcohol in $CH_2Cl_2$ as eluent (Merck silica gel caused significant decomposition during the purification). This afforded 97 mg (40%) of clear oil, whose 'H NMR spectral properties were consistent with the structure of 20.

Compound 20 was oxidized to 21 as described for 3. Compound 21 was coupled with amine 22 and subsequently converted into the phosphonate 24 in a similar manner to that described for compound 3.

The FMOC group can be substituted using conventional methods.

EXAMPLE 4

Preparation of Cme(O—$CH_2$—$CH_2$—NR)T

The compounds used and generated in this example are shown in Scheme 4, FIG. 4.

To a solution of 25 (1.63 g, 3.00 mmol) in THF (10 ml) was added NaH (420 mg, 60% dispersion in oil), and the solution was stirred for 1 hour. Allyl iodide (0.30 ml) was added, and the solution was stirred for an additional 4 hours. The reaction mixture was poured in 5% aqueous bicarbonate, and the crude product was extracted with MC, washed with saturated brine, dried over sodium sulfate, and concentrated to deliver the product 26 as a crisp yellow foam (1.69 g).

Compound 26 was converted into aldehyde 28 in a manner previously described for compound 3. Aldehyde 28 was coupled with compound 5 and subsequently converted to the phosphonate 30 in a manner previously described for compound 6.

The FMOC group can be substituted using conventional methods.

EXAMPLE 5

Preparation of Morpholine C($CH_2CH_2$—O)T

A. Preparation of $H_2N$—$CH_2$—$CH_2$—O—Si(Me)t—bu Linker.

5 ml of ethanol amine and 5 ml pyridine were evaporated with vacuum, 10 ml pyridine was added, and 3 g of dimethyl t-butyl silyl chloride was added. The reaction was stirred or 16 hours at 20° C. The reaction was diluted into methylene chloride and extracted 2× with sodium phosphate buffer, pH 9. The organic layer was dried with $Na_2SO_4$ and evaporated to dryness under vacuum to yield the desired linker.

B. Preparation of silyl-protected hydroxyethyl morpholino cytidine.

1.2 g of cytidine was dissolved in 25 ml water and 1.15 g of sodium periodate added and the solution stirred for 16 hours at 20° C. The solvent was evaporated using vacuum and the crude product suspended in 10 ml methanol. 0.26 ml of acetic acid was added along with 1.9 g of O-dimethyl t-butyl silyl ethanol amine (from part A) and 0.59 g of sodium cyanoborohydride. This was stirred for 16 hours at 20° C. The reaction was extracted with methylene chloride after the addition of sodium phosphate buffer, pH 9. The organic layer was dried using $Na_2SO_4$, the solvent evaporated using vacuum, and the residue purified by silica gel chromatography using acetonitrile as the eluant and a gradient up to 10% $H_2O$ to elute the product.

C. Preparation of 5'Dimethoxytrityl hydroxyethyl morpholino N-benzoyl cytidine.

0.55 g of silyl-protected hydroxyethyl morpholino cytidine from part B was treated with 0.6 ml of trimethyl silyl chloride in 10 ml of pyridine for 30 minutes. 0.16 ml of benzoyl chloride was then added and the reaction stirred for 30 minutes and then extracted in methylene chloride and sodium phosphate buffer, pH 9. The organic layer was dried with $Na_2SO_4$ and evaporated under vacuum. The residue was evaporated from pyridine and then dissolved in 5 ml of pyridine and treated with 0.45 g of dimethoxy trityl chloride. The residue was diluted after 1 hour with methylene chloride and extracted against sodium phosphate buffer, pH 9. The organic layer was dried with $Na_2SO_4$ and then evaporated under vacuum. The residue was dissolved in toluene and reevaporated and then treated with 5 ml of 0.7 molar tetrabutyl ammonium fluoride in THF to yield the title compound. This was then evaporated under vacuum after 1 hour and purified by silica gel chromatography using methylene chloride as the eluant and a gradient to 10% isopropanol.

D. Generation of the Aldehyde

The product compound of part C (58 mg) was dissolved in 250 μl benzene and 250 μl DMSO, 8 μl pyridine and 4 μl trifluoroacetic acid followed by 60 mg of dicyclohexyl carbodiimide. After 48 hours at 20° C., the reaction was diluted with methylene chloride and extracted with sodium bicarbonate solution. The organic layer was dried with $Na_2SO_4$, evaporated in vacuum and dissolved and evaporated from acetonitrile and toluene. The aldehyde was used directly.

E. Reductive Coupling to 5' amino thymidine.

Reductive alkylation, 3' desilylation, nitrogen protection with FMOC, 3' phosphitilation and coupling into oligonucleotides was performed as described for the other analogs.

EXAMPLE 6

Preparation of 5'—TCTCme($CH_2$—$CH_2$—NH)TCme($CH_2$—$CH_2$—NH)TCme($CH_2$—$CH_2$—NH)TCme($CH_2$—$CH_2$—NH)TTTT—3'

The oligomer of this example was synthesized using the conventional techniques described by Froehler, B. C. et al., *Nucleic Acids Res* (1986) 14:5399, but with the incorporation of the Cme($CH_2$—$CH_2$—NFMOC)T dimer synthon. This dimer was constructed using the technique described in Example 1. The oligomers resulting from the synthesis were deblocked with concentrated ammonia for 16 hours at 20° C. and gel purified using conventional techniques.

EXAMPLE 7

Preparation of 5'—TCTCme(O—$CH_2$—$CH_2$—NH)TCme(O—$CH_2$—$CH_2$—NH)TCme(O—$CH_2$—$CH_2$—NH)TCme(O—$CH_2$—$CH_2$—NH)TTTT—3'

The oligomer of this example was synthesized as in Example 6, using the conventional techniques described by Froehler, B. C. et al., *Nucleic Acids Res* (1986) 14:5399, but with the incorporation of the Cme(O—$CH_2$—$CH_2$—NFMOC)T dimer synthon. This dimer was constructed using the technique described in Example 4. The oligomers resulting from the synthesis were deblocked with concentrated ammonia for 16 hours at 20° C. and gel purified using conventional techniques.

EXAMPLE 8

Preparation of 5'—TCTCTC($CH_2$—$CH_2$—O)TC($CH_2$—$CH_2$—O)TCTTTT—3'

The oligomer prepared in this example consisted of conventional nucleotides as well as modified internucleoside linkages wherein the C preceeding each of the modified linkers was a hydroxyethyl morpholino cytidine. This oligomer was synthesized as in Example 6, using the conventional techniques described by Froehler, B. C. et al., *Nucleic Acids Res* (1986) 14:5399, but with the incorporation of the morpholine C($CH_2$—$CH_2$—O)T dimer synthon. This dimer was constructed using the technique described in Example 5. The oligomers resulting from the synthesis were deblocked with concentrated ammonia for 16 hours at 20° C. and gel purified using conventional techniques.

EXAMPLE 9

Hybridization to Complementary RNA

RNA sequences complementary to the compounds synthesized in Examples 6, 7 and 8 were generated using T7 transcription (Milligan, T. F., et al., *Nucleic Acids Res* (1987) 15:8783). These RNAs were used to test the ability of each of the compounds to hybridize to its complement as compared to analogous sequences wherein the modified linkages were replaced by phosphodiesters. The melting temperatures of complexes formed with the compounds and these controls were measured using 100 mM NaCl, 50 mM Tris, pH 7.5 under standard conditions as described by Summers, M. F., et al., Nucleic Acids Res (1986) 14:7421. The results are shown in Table 2, where nucleosides separated by * represent the nucleosides separated by the modified linkages described in the examples.

TABLE 2

| | Tm |
|---|---|
| TCTCme*TCme*TCme*TCme*TTTT (example 6) | 62.0 |
| TCTCme*TCme*TCme*TCme*TTTT (example 7) | 50.5 |
| TCTCmeTCmeTCmeTCmeTTTT | 61.5 |
| TCTCTC*TC*TCTTTT (example 8) | 51.5 |
| TCTCTCTCTCTTTT | 57.0 |

As shown in Table 2, the oligomer containing the modified linkage of Example 6 binds better than the control and that of Example 8 binds nearly as well as the diester control.

EXAMPLE 10

Binding to Duplex DNA

The "footprint" assay described by Cooney, M. et al., *Science* (1988) 241:456 was used to show the ability of the modified oligomers to bind duplex DNA. The assay is based on the ability of the oligomer bound to duplex to protect the duplex from digestion with DNAse I. Various concentrations of the test oligomer ranging from 0.1–10 uM were incubated with a $p^{32}$ radiolabeled restriction fragment bearing the target sequence at 1 nM concentration in 10 mM NaCl, 140 mM KCl, 1 mM $MgCl_2$, 1 mM spermine and 20 mM MOPS buffer at pH 7 for 2 hours. The target sequences for the oligomers prepared in these examples were the same as in Table 2.

DNAse I was added to permit limited digestion, the samples were then denatured and subjected to polyacrylamide gel electrophoresis which separates the DNA fragments based on size.

Figure 16:
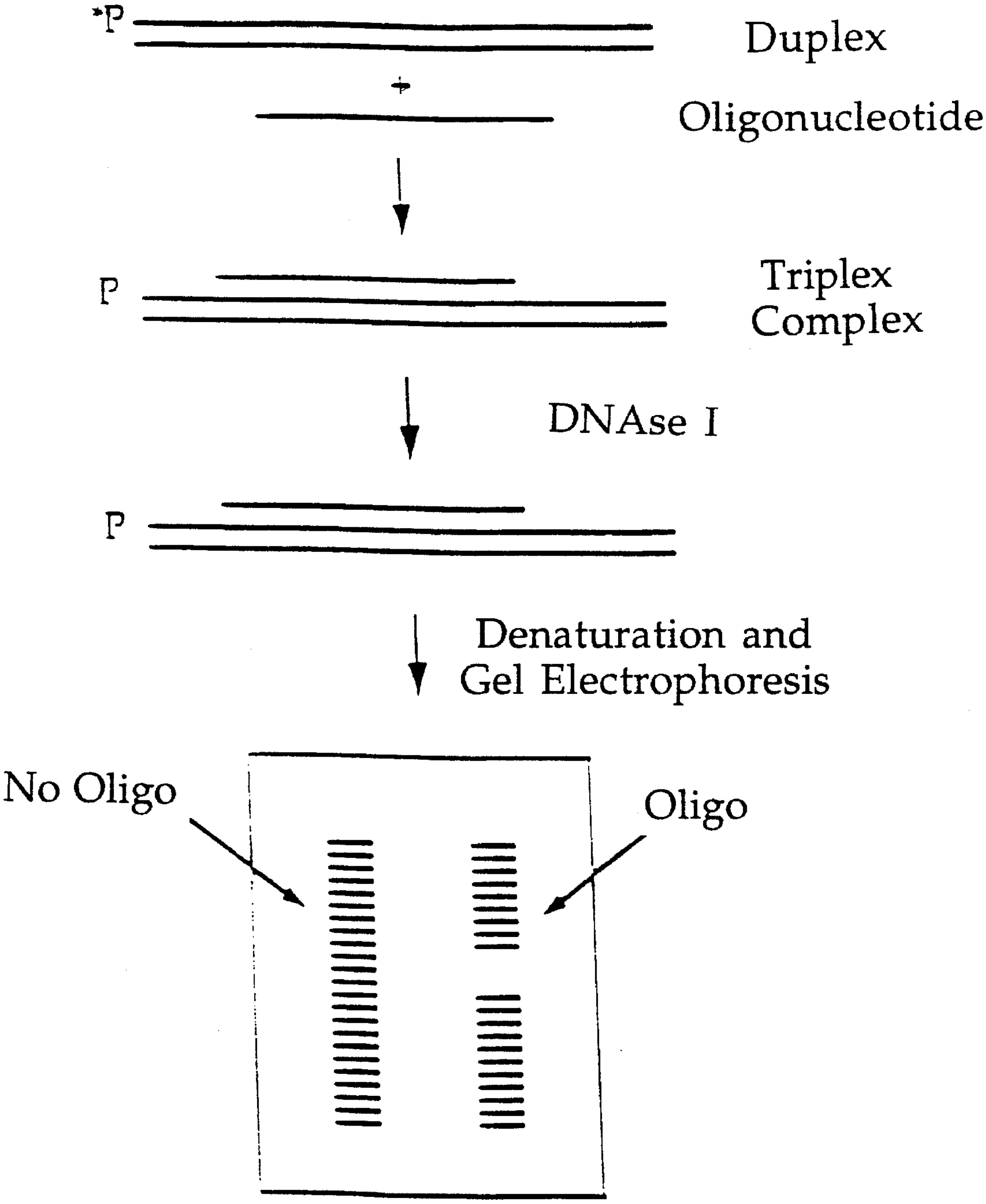
FIG. 16 shows an outline of, and idealized results of, the footprint assay for DNA-duplex binding.

An outline of the principle of the footprint assay and idealized results are shown in FIG. 16. As shown in FIG. 16, the labeled duplex, when treated with DNAse, should yield lengths of oligomer corresponding to cleavage at each diester linkage, thus obtaining the series of bands shown on the left in the idealized gel. On the other hand, when the duplex is protected by binding to the oligomer, the series of lengths represented by cleavage at the diester linkages in the region protected by binding to the oligomer is missing from the gel. This "footprint" indicates the region of protection. The results are semiquantitatively estimated by observing either the complete absence of, or only weak appearance of, bands in the region of the footprint.

The modified oligomers and the phosphodiester oligomer showed more than 90% protection at 1 μM concentration of the oligomer. Thus, the modified oligomers and conventional oligomers appeared to have similar affinity for the duplex.

EXAMPLE 11

Preparation of T (NR—$CH_2$—$CH_2$) T

The preparation of alkyl derivatives of the 3' amine, as shown in Scheme 13, FIG. 13 began with azide 10. Compound 10 (3.0 g, 5.3 mmol) in methanol (50 ml) with 10% palladium on carbon (1.0 g) was hydrogenated at 200 psi for 18 h. The catalyst was removed by filtration and the solvent by rotary evaporation to deliver the amine (2.3 g, 75%) 80. To a solution of amine 81 (1.26 g, 2.32 mmol), acetaldehyde (0.79 ml, 3.01 mmol), and toluene (25 mmol) was added titanium isopropoxide (0.90 ml, 3.01 mmol), and the solution was stirred for 2 h. At this point absolute ethanol (25 mmol) and sodium cyanoborohydride were added. The mixture was subsequently stirred for 18 h and stripped to dryness.

The crude product was chromatographed on silica gel (1% $Et_3N$/3 to 5 to 8% 2-propanol/MC) to deliver the product (1.04 g, 78.5%) as a crisp white foam. In a similar manner, amines 82 and 83 were prepared. Compounds 81–83 were then coupled with aldehyde 16 as described for amine 12 to deliver dimers 84–86, which were then converted to the corresponding phosphonates 89 as described for compound 18.

The preparation of acylated derivatives of the 3' amine began with the dimer 90, which was prepared as described for compound 17. Dimer 90 was deprotected with tetrabutylammonium fluoride as described for compound 7 to yield dimer 91. To a solution of amine 91 (200 mg, 0.25 mmol), ethyl acetate (5 ml) and 5% aqueous sodium bicarbonate (5 ml) was added ethyl chloroformate (30 μL, 0.31 mmol). The organic layer was separated, dried over sodium sulfate, and concentrated. The crude product was chromatographed on silica gel (3 to 5 to 10 to 15% 2propanol/MC) to yield the product 92 (185 mg, 85%). Likewise, carbamate 93 was prepared. Compounds 92 and 93 were subsequently converted to the phosphonates 94 and 95 as described for compound 18.

EXAMPLE 12

Preparation of morpholine T ($CH_2$) T

The morpholino derivative 97 shown in Scheme 14, FIG. 14, was prepared from the protected 5-methyluridine 96. To a solution of diol 96 (5.90 g, 10.5 mmol), ammonium acetate (4.06 g, 52.6 mmol) and methanol was added sodium periodate (2.25 g, 10.5 mmol). The mixture was stirred for 1 h and filtered; sodium cyanoborohydride (1.32 g, 21 mmol) was subsequently added to the filtrate. The solution was then stirred for 18 h and concentrated. The crude product was partitioned between methylene chloride and aqueous sodium phosphate (pH 9.0), and the organic layer was concentrated. The product was chromatographed on silica gel (3 to 5 to 8% methanol/MC) to deliver a crisp white foam 97 (5.05 g, 88%). Morpholine 97 was reacted with aldehyde 16 to form the dimer, and subsequently converted to the phosphonate 98 as described for compound 18.

The aminal derivative 101 was prepared from amine 80, which was acylated with ethyl chloroformate to give carbamate 99. The carbamate 99 was alkylated with chloromethyl methylsulfide in the presence of sodium hydride to afford thioaminal 100. Compound 100 was activated with bromine in the presence of alcohol 31 to deliver dimer 101, which was then converted to the corresponding phosphonate 102 as described for compound 18.

EXAMPLE 13

Preparation of T—(S—$CH_2$—$CH_2$)—T

The compounds used and generated in this example are shown in Scheme 15, FIG. 15. To a solution of alcohol 46 (0.79 g, 2.0 mmol) in DMF (10 mL) and pyridine (5 mL) was added methylthiophenoxyphosphonium iodide, and the reaction was stirred for 3 h. The reaction was quenched with methanol (5 mL) and the solvents removed on the rotary evaporator. The crude product was dissolved in methylene chloride; extracted with aqueous saturated sodium thiosulfate and aqueous saturated sodium bicarbonate; dried; concentrated; and chromatographed on silica gel to deliver the iodide 103 (0.36 g).

To a solution of thiol 42 (0.25 g, 0.37 mmol) and acetonitrile (10 mL) was added bis(trimethylsilyl) acetamide. After 30 min the solvent was evaporated; DMF (5 mL) and iodide 103 (0.20 g, 0.41 mmol) were added. The reaction was stirred for 3 h and then quenched with aqueous saturated sodium bicarbonate. The crude product was extracted with methylene chloride; dried; concentrated; and chromatographed on silica gel to deliver dimer 104. Dimer 104 was converted to the phosphorate LOS as descried for compound 18.

Although preferred embodiments of the subject invention have been described in some detail, it is understood that obvious variations can be made without departing from the spirit and the scope of the invention as defined by the appended claims.

We claim:

1. A dimer of the formula

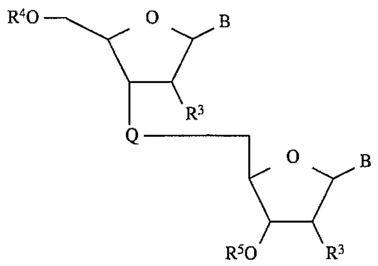

wherein $R^3$ is independently H, OH, $OCH_3$, $SCH_3$, $OC_3H_5$, $OC_3H_7$, $SC_3H_7$, or F;

$R^4$ is hydrogen or a hydroxyl protecting group;

$R^5$ is hydrogen, a solid support or a hydroxyl protecting group;

B is independently a purine or pyrimidine residue or an analogous protected residue, and wherein Q is —N(R)—$CH_2$—CH—, —$CH_2$—N(R)—$CH_2$— or —$CH_2$—$CH_2$—N(R)— wherein the left bond of each Q group is bonded to the 3' position of the structure (1) nucleotide and the right bond of each Q group is bonded to the 5' position of the adjacent structure (1.) nucleoside, wherein R is hydrogen, methyl, ethyl, FMOC, methoxymethyl or —C(O)—O—$CH_2$—$CH_3$.

2. The dimer of claim 1 wherein Q is —$CH_2$—$CH_2$—N(R)—.

3. The dimer of claim 1 wherein R is hydrogen, methyl, or FMOC.

4. The dimer of claim 1 wherein $R^4$ is DMTO or phosphate.

5. The dimer of claim 1 wherein $R^5$ is a t-butyldimethylsilyl, phosphonate or a phosphoramidate group.

6. The dimer of claim 5 wherein the phosphonate group is H-phosphonate.

7. The dimer of claim 1 wherein B is a protected base.

8. An oligomer of the formula (1)

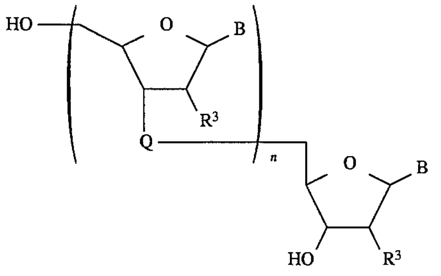

wherein each $R^3$ is independently H, OH, $OCH_3$, $SCH_3$, $OC_3H_5$ (O-allyl), $OC_3H_7$ (O-propyl), $SC_3H_7$, or F, and wherein each B is independently a purine or pyrimidine residue or an analogous residue, and wherein at least one Q is a modified internucleoside linkage of structure —N(R)—$CH_2$—$CH_2$—, —$CH_2$—N(R)—$CH_2$—or —$CH_2$—$CH_2$—N(R)— wherein the left bond of each O group is bonded to the Y position of the structure (1) nucleoside and the right bond of each O group is bonded to the 5' position of the adjacent Structure (1) nucleoside, wherein R is hydrogen, methyl, ethyl, methoxymethyl, FMOC or —C(O)—O—$CH_2$—$CH_3$, and the remaining Q are a phosphodiester analog, wherein the modified internucleoside linkage alternates in a regular pattern comprising one modified internucleoside linkage followed by two phosphodiester analog linkages; and n is an integer between 1 and 200.

9. The oligomer of claim 8 wherein the phosphodiester analog is a phosphorothioate linkage.

10. The oligomer of claim 8 wherein Q is —$CH_2$—$CH_2$—N(R)—.

11. The oligomer of claim 10 wherein R is hydrogen or FMOC.

12. An oligomer having the formula (1)

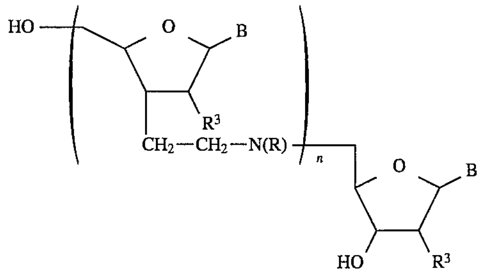

wherein each $R^3$ is independently H, OH, $OCH_3$, $SCH_3$, $OC_3H_5$ (O-allyl), $OC_3H_7$ (O-propyl), $SC_3H_7$, or F, and wherein each B is independently a purine or pyrimidine residue or an analogous residue;

R is H or FMOC; and n is an integer between 1 and 200.

* * * * *